(12) United States Patent
Namai

(10) Patent No.: US 9,465,291 B2
(45) Date of Patent: Oct. 11, 2016

(54) RADIATION-SENSITIVE RESIN COMPOSITION, POLYMER, COMPOUND, AND METHOD FOR PRODUCING COMPOUND

(71) Applicant: JSR CORPORATION, Tokyo (JP)

(72) Inventor: Hayato Namai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/200,505

(22) Filed: Mar. 7, 2014

(65) Prior Publication Data

US 2014/0186771 A1 Jul. 3, 2014

Related U.S. Application Data

(63) Continuation of application No. PCT/JP2012/083754, filed on Dec. 26, 2012.

(30) Foreign Application Priority Data

Dec. 28, 2011 (JP) ................................ 2011-290144
Jul. 9, 2012 (JP) ................................ 2012-154159

(51) Int. Cl.

| | |
|---|---|
| *G03F 7/039* | (2006.01) |
| *G03F 7/20* | (2006.01) |
| *G03F 7/26* | (2006.01) |
| *C07D 307/93* | (2006.01) |
| *C07C 69/54* | (2006.01) |
| *C07D 333/78* | (2006.01) |
| *C08F 20/10* | (2006.01) |
| *C07D 307/935* | (2006.01) |
| *C07D 307/77* | (2006.01) |
| *C08F 220/40* | (2006.01) |
| *C08F 22/10* | (2006.01) |

(Continued)

(52) U.S. Cl.

CPC ............. *G03F 7/0392* (2013.01); *C07C 69/54* (2013.01); *C07D 307/33* (2013.01); *C07D 307/77* (2013.01); *C07D 307/93* (2013.01); *C07D 307/935* (2013.01); *C07D 317/36* (2013.01); *C07D 317/70* (2013.01); *C07D 333/78* (2013.01); *C07D 491/056* (2013.01); *C07D 493/04* (2013.01); *C08F 20/10* (2013.01); *C08F 22/10* (2013.01); *C08F 220/28* (2013.01); *C08F 220/40* (2013.01); *C08L 33/14* (2013.01); *G03C 1/73* (2013.01); *G03F 7/0397* (2013.01); *G03F 7/11* (2013.01); *G03F 7/20* (2013.01); *G03F 7/2041* (2013.01); *G03F 7/38* (2013.01); *C07C 2101/08* (2013.01); *C07C 2101/10* (2013.01); *C07C 2101/14* (2013.01); *C07C 2101/16* (2013.01); *C07C 2102/28* (2013.01); *C07C 2102/42* (2013.01)

(58) Field of Classification Search

None
See application file for complete search history.

(56) References Cited

U.S. PATENT DOCUMENTS 4,000,958 A * 1/1977 Hirooka et al. .............. 427/389
4,910,122 A    3/1990 Arnold et al.

(Continued)

FOREIGN PATENT DOCUMENTS

| JP | 06-12452 | 5/1984 |
|---|---|---|
| JP | 59-93448 | 5/1984 |

(Continued)

OTHER PUBLICATIONS

Sugiyama et al (Accession No. 1979:23279 and English abstract of article from Kinki Daigaku Kogakubu Kenkyu Hokoku from 1977) pp. 2-3 only.*

(Continued)

*Primary Examiner* — Cynthia Hamilton
(74) *Attorney, Agent, or Firm* — Oblon, McClelland, Maier & Neustadt, L.L.P.

(57) ABSTRACT

A radiation-sensitive resin composition includes a polymer that includes a structural unit represented by a formula (1), and an acid generator. $R^1$ is a hydrogen atom, a fluorine atom, or the like. $R^2$ is a hydrogen atom or a monovalent hydrocarbon group. $R^3$ is a hydrogen atom, a monovalent chain hydrocarbon group, or the like. $R^4$ is a hydrogen atom, a monovalent chain hydrocarbon group, or the like. $R^5$ is a hydrogen atom, a monovalent chain hydrocarbon group, or the like. $R^6$ is a monovalent chain hydrocarbon group. $R^6$ is bonded to $R^3$ to form a first alicyclic structure, or $R^6$ is bonded to $R^5$ to form a second alicyclic structure. At least one hydrogen atom of $R^2$, $R^3$, or $R^4$ is optionally substituted with a fluorine atom.

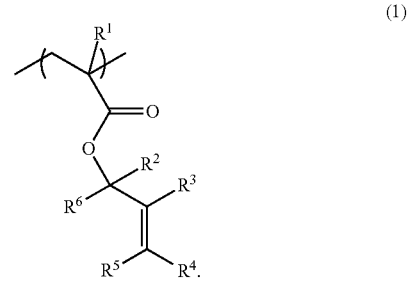

(1)

17 Claims, No Drawings

(51) Int. Cl.
*G03C 1/73* (2006.01)
*G03F 7/11* (2006.01)
*G03F 7/38* (2006.01)
*C08F 220/28* (2006.01)
*C08L 33/14* (2006.01)
*C07D 317/36* (2006.01)
*C07D 317/70* (2006.01)
*C07D 491/056* (2006.01)
*C07D 493/04* (2006.01)
*C07D 307/33* (2006.01)

(56) References Cited

U.S. PATENT DOCUMENTS

| 5,443,690 | A | * | 8/1995 | Takechi et al. | 430/286.1 |
| 5,554,496 | A | * | 9/1996 | Shiratsuchi et al. | 430/536 |
| 6,060,207 | A | * | 5/2000 | Shida et al. | 430/176 |
| 2009/0042147 | A1 | * | 2/2009 | Tsubaki | 430/326 |

FOREIGN PATENT DOCUMENTS

| JP | 10-140018 | | 5/1998 |
| JP | 2000-128930 | | 5/2000 |
| JP | 2007-140289 | | 6/2007 |
| JP | 2007-304537 | | 11/2007 |
| JP | 2008-088343 | | 4/2008 |
| JP | 2008-304902 | | 12/2008 |
| JP | 2009-276607 | | 11/2009 |
| JP | 2010-122579 | | 6/2010 |
| JP | 2011-013419 | | 1/2011 |
| JP | 2011-141471 | A * | 7/2011 |
| WO | WO 2007/116664 | | 10/2007 |

OTHER PUBLICATIONS

CAS Registry No. 68754-13-2, from SciFinder database downloaded Mar. 6, 2015, 3 pages.*
Miller et al , Organic Letters, vol. 4, No. 16, pp. 2743-2745, year 2002, published on WEB Jul. 13, 2002.*
Accession No. 1996:190901, CAN 124:302576, Abstract and substances set forth for U.S. Pat. No. 6060207 and attached some of Substance registry numbers and structures assigned to said abstract by Chemical Abstracts service. downloaded Apr. 29, 2015 from SciFinder database.*
Eagleson (Concise Encyclopedia Chemistry 1994) entry "Pyretherins" pp. 912-913.*
English translation of JP, 2000-128930, A (2000) from machine translation from AIPN Japan Patent Office National Center for Industrial Property Information and Training, generated Mar. 6, 2015, 50 pages.*
Ferret et al "Acryloxy and Methacryloxy Palladation of Alkenes", J. CHemi. SOc. Chem. Commun. 1994, pp. 2589-2590.*
Nishikubo et al., "Convenient Syntheses of Cyclic Carbonates by New Reaction of Oxiranes with beta-Butyrolactone", Tetrahedron Letters, 1986, pp. 3741-3744, vol. 27, No. 32.
Calo et al., "Cyclic Carbonate Formation from Carbon Dioxide and Oxiranes in Tetrabutylammonium Halides as Solvents and Catalysts", Organic Letters, 2002, pp. 2561-2563, vol. 4, No. 15.
International Search Report for corresponding International Application No. PCT/JP2012/083754, Mar. 26, 2013.
Office Action issued Aug. 2, 2016, in Japanese Patent Application No. 2013-551763 (w/ English translation).
T. Iizawa et al., Synthesis and Photochemical Reaction of Polymers Containing Pendant 2-Cyclohexenone-4-yl Ester, Journal of Photopolymer Science and Technology, The Society of Photopolymer Science and Technology, 1990, vol. 3, No. 2, pp. 125-126.

* cited by examiner

RADIATION-SENSITIVE RESIN COMPOSITION, POLYMER, COMPOUND, AND METHOD FOR PRODUCING COMPOUND

CROSS-REFERENCE TO RELATED APPLICATIONS

The present application is a continuation application of International Application No. PCT/JP2012/083754, filed Dec. 26, 2012, which claims priority to Japanese Patent Application No. 2011-290144, filed Dec. 28, 2011, and to Japanese Patent Application No. 2012-154159, filed Jul. 9, 2012. The contents of these applications are incorporated herein by reference in their entirety.

BACKGROUND OF THE INVENTION

1. Field of the Invention

The invention relates to a radiation-sensitive resin composition, a polymer, a compound, and a method for producing a compound.

2. Discussion of the Background

In the field of microfabrication such as production of integrated circuit devices, a fine resist pattern may be formed by forming a resist film on a substrate using a radiation-sensitive resin composition that includes an acid-labile group-containing polymer, exposing the resist film by applying short-wavelength radiation (e.g., excimer laser light) to the resist film via a mask pattern, and removing the exposed area using an alkaline developer. The above process may utilize a radiation-sensitive resin composition that includes a photoacid generator that generates an acid upon irradiation, and exhibits improved sensitivity due to the acid.

When using such a radiation-sensitive resin composition, post-exposure bake (PEB) may be performed in order to promote dissociation of the acid-labile group, and ensure that the exposed area exhibits sufficient solubility in an alkaline developer. The PEB temperature is normally set to about 90 to 180° C. However, while dissociation of the acid-labile group sufficiently occur when using such a PEB temperature, diffusion of an acid into the unexposed area may occur significantly, and affect the pattern-forming capability of the radiation-sensitive resin composition. In particular, since the line width of the resist pattern was been reduced to 90 nm or less, it may be difficult to obtain a resist pattern that has a good pattern shape, and has small line width roughness (LWR) (i.e., an index that indicates a variation in line width).

The above problem may be solved by suppressing the acid diffusion speed by reducing the PEB temperature. In recent years, it has been desired to reduce energy consumption during the production process by reducing the PEB temperature from the viewpoint of reducing the environmental impact and the production cost.

However, when the PEB temperature is reduced, the dissociation rate of the acid-labile group may decrease, and the resist film in the exposed area may not be sufficiently dissolved. As a result, the pattern-forming capability of the radiation-sensitive resin composition may deteriorate. Therefore, a technique has been studied that makes it possible to reduce the PEB temperature by designing an acid-labile group that easily undergoes dissociation. For example, a positive-tone photosensitive resin composition that includes a resin that includes an acid-labile group having a specific acetal structure (see Japanese Patent Application Publication (KOKAI) No. 2008-304902), and a positive-tone resist composition that includes a resin that includes a structural unit including a tertiary ester structure and a structural unit including a hydroxyalkyl group (see Japanese Patent Application Publication (KOKAI) No. 2009-276607), have been proposed.

SUMMARY OF THE INVENTION

According to one aspect of the present invention, a radiation-sensitive resin composition includes a polymer that includes a structural unit represented by a formula (1), and an acid generator.

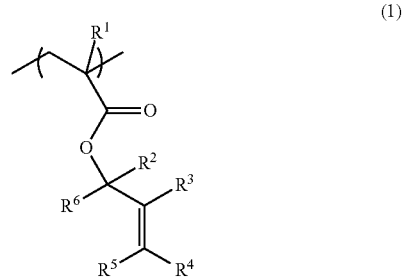

(1)

$R^1$ is a hydrogen atom, a fluorine atom, a methyl group, or a trifluoromethyl group; $R^2$ is a hydrogen atom or a monovalent hydrocarbon group; $R^3$ is a hydrogen atom, a monovalent chain hydrocarbon group, a monovalent alicyclic hydrocarbon group, or a monovalent aromatic hydrocarbon group, and $R^3$ is optionally bonded to $R^6$ to form a first alicyclic structure together with the carbon atom bonded to $R^3$ and with the carbon atom bonded to $R^6$; $R^4$ is a hydrogen atom, a monovalent chain hydrocarbon group, a monovalent alicyclic hydrocarbon group, or a monovalent aromatic hydrocarbon group; $R^5$ is a hydrogen atom, a monovalent chain hydrocarbon group, a monovalent alicyclic hydrocarbon group, or a monovalent aromatic hydrocarbon group, and $R^5$ is optionally bonded to $R^6$ to form a second alicyclic structure together with the carbon atom bonded to $R^5$, with the carbon atom bonded to $R^3$ and with the carbon atom bonded to $R^6$; $R^6$ is a monovalent chain hydrocarbon group; $R^6$ is bonded to $R^3$ to form the first alicyclic structure together with the carbon atom bonded to $R^6$ and with the carbon atom bonded to $R^3$, or $R^6$ is bonded to $R^5$ to form the second alicyclic structure together with the carbon atom bonded to $R^6$, with the carbon atom bonded to $R^3$ and with the carbon atom bonded to $R^5$; and at least one hydrogen atom of $R^2$, $R^3$, or $R^4$ is optionally substituted with a fluorine atom. In a case where $R^6$ and $R^5$ are bonded to each other to form the second alicyclic structure, $R^2$ is a hydrogen atom; $R^3$ is a hydrogen atom, a monovalent chain hydrocarbon group, a monovalent alicyclic hydrocarbon group, or a monovalent aromatic hydrocarbon group; and optionally, $R^3$ and $R^4$ are bonded to each other to form an alicyclic structure or an aromatic heterocyclic structure together with the carbon atom bonded to $R^3$ and with the carbon atom bonded to $R^4$, or $R^4$ and $R^5$ are bonded to each other to form an alicyclic structure or an aromatic heterocyclic structure together with the carbon atom bonded to $R^4$ and with the carbon atom bonded to $R^5$.

According to one aspect of the present invention, a resist pattern-forming method includes forming a resist film on a substrate using the radiation-sensitive resin composition. The resist film is exposed. The exposed resist film is heated. The heated resist film is developed.

According to further aspect of the present invention, a polymer includes a structural unit represented by a formula (1).

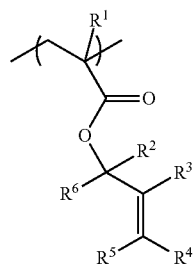
(1)

$R^1$ is a hydrogen atom, a fluorine atom, a methyl group, or a trifluoromethyl group; $R^2$ is a hydrogen atom or a monovalent hydrocarbon group; $R^3$ is a hydrogen atom, a monovalent chain hydrocarbon group, a monovalent alicyclic hydrocarbon group, or a monovalent aromatic hydrocarbon group, and $R^3$ is optionally bonded to $R^6$ to form a first alicyclic structure together with the carbon atom bonded to $R^3$ and with the carbon atom bonded to $R^6$; $R^4$ is a hydrogen atom, a monovalent chain hydrocarbon group, a monovalent alicyclic hydrocarbon group, or a monovalent aromatic hydrocarbon group; $R^5$ is a hydrogen atom, a monovalent chain hydrocarbon group, a monovalent alicyclic hydrocarbon group, or a monovalent aromatic hydrocarbon group, and $R^5$ is optionally bonded to $R^6$ to form a second alicyclic structure together with the carbon atom bonded to $R^5$, with the carbon atom bonded to $R^3$ and with the carbon atom bonded to $R^6$; $R^6$ is a monovalent chain hydrocarbon group; $R^6$ is bonded to $R^3$ to form the first alicyclic structure together with the carbon atom bonded to $R^6$ and with the carbon atom bonded to $R^3$, or $R^6$ is bonded to $R^5$ to form the second alicyclic structure together with the carbon atom bonded to $R^6$, with the carbon atom bonded to $R^3$ and with the carbon atom bonded to $R^5$; and at least one hydrogen atom of $R^2$, $R^3$, or $R^4$ is optionally substituted with a fluorine atom. In a case where $R^6$ and $R^5$ are bonded to each other to form the second alicyclic structure, $R^2$ is a hydrogen atom; $R^3$ is a hydrogen atom, a monovalent chain hydrocarbon group, a monovalent alicyclic hydrocarbon group, or a monovalent aromatic hydrocarbon group; and optionally, $R^3$ and $R^4$ are bonded to each other to form an alicyclic structure or an aromatic heterocyclic structure together with the carbon atom bonded to $R^3$ and with the carbon atom bonded to $R^4$, or $R^4$ and $R^5$ are bonded to each other to form an alicyclic structure or an aromatic heterocyclic structure together with the carbon atom bonded to $R^4$ and with the carbon atom bonded to $R^5$.

According to further aspect of the present invention, a compound is represented by a formula (i).

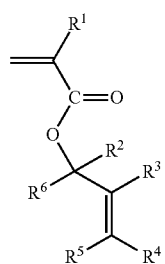
(i)

$R^1$ is a hydrogen atom, a fluorine atom, a methyl group, or a trifluoromethyl group; $R^2$ is a hydrogen atom or a monovalent hydrocarbon group; $R^3$ is a hydrogen atom, a monovalent chain hydrocarbon group, a monovalent alicyclic hydrocarbon group, or a monovalent aromatic hydrocarbon group, and $R^3$ is optionally bonded to $R^6$ to form a first alicyclic structure together with the carbon atom bonded to $R^3$ and with the carbon atom bonded to $R^6$; $R^4$ is a hydrogen atom, a monovalent chain hydrocarbon group, a monovalent alicyclic hydrocarbon group, or a monovalent aromatic hydrocarbon group; $R^5$ is a hydrogen atom, a monovalent chain hydrocarbon group, a monovalent alicyclic hydrocarbon group, or a monovalent aromatic hydrocarbon group, and $R^5$ is optionally bonded to $R^6$ to form a second alicyclic structure together with the carbon atom bonded to $R^5$, with the carbon atom bonded to $R^3$ and with the carbon atom bonded to $R^6$; $R^6$ is a monovalent chain hydrocarbon group; $R^6$ is bonded to $R^3$ to form the first alicyclic structure together with the carbon atom bonded to $R^6$ and with the carbon atom bonded to $R^3$, or $R^6$ is bonded to $R^5$ to form the second alicyclic structure together with the carbon atom bonded to $R^6$, with the carbon atom bonded to $R^3$ and with the carbon atom bonded to $R^5$; and at least one hydrogen atom of $R^2$, $R^3$, or $R^4$ is optionally substituted with a fluorine atom. In a case where $R^6$ and $R^5$ are bonded to each other to form the second alicyclic structure, $R^2$ is a hydrogen atom; $R^3$ is a hydrogen atom, a monovalent chain hydrocarbon group, a monovalent alicyclic hydrocarbon group, or a monovalent aromatic hydrocarbon group; and optionally, $R^3$ and $R^4$ are bonded to each other to form an alicyclic structure or an aromatic heterocyclic structure together with the carbon atom bonded to $R^3$ and with the carbon atom bonded to $R^4$, or $R^4$ and $R^5$ are bonded to each other to form an alicyclic structure or an aromatic heterocyclic structure together with the carbon atom bonded to $R^4$ and with the carbon atom bonded to $R^5$.

According to further aspect of the present invention, a method for producing a compound represented by a formula (i), includes reacting a cyclic α,β-unsaturated ketone represented by a formula (a) with an organolithium compound represented by a formula (b) or a hydrogenation agent to obtain a cyclic unsaturated alcohol represented by a formula (c). The cyclic unsaturated alcohol represented by the formula (c) is reacted with a compound represented by a formula (d).

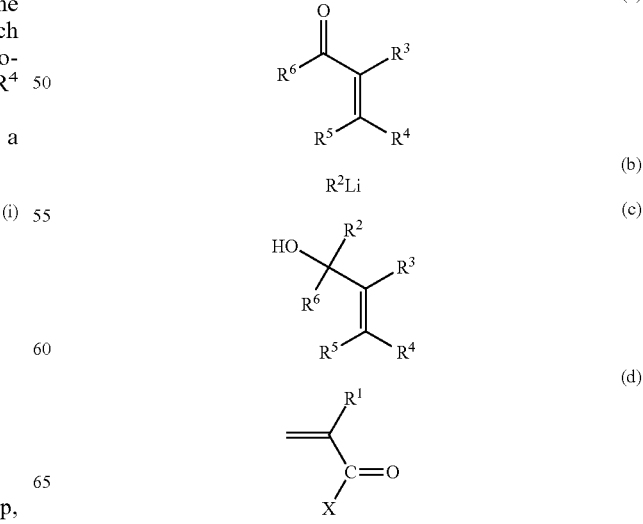

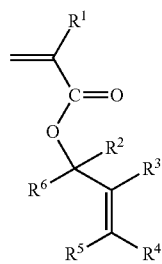

(i)

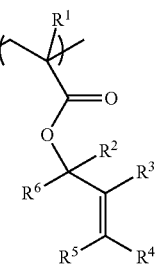

(1)

$R^1$ is a hydrogen atom, a fluorine atom, a methyl group, or a trifluoromethyl group; $R^2$ is a hydrogen atom or a monovalent hydrocarbon group; $R^3$ is a hydrogen atom, a monovalent chain hydrocarbon group, a monovalent alicyclic hydrocarbon group, or a monovalent aromatic hydrocarbon group, and $R^3$ is optionally bonded to $R^6$ to form a first alicyclic structure together with the carbon atom bonded to $R^3$ and with the carbon atom bonded to $R^6$; $R^4$ is a hydrogen atom, a monovalent chain hydrocarbon group, a monovalent alicyclic hydrocarbon group, or a monovalent aromatic hydrocarbon group; $R^5$ is a hydrogen atom, a monovalent chain hydrocarbon group, a monovalent alicyclic hydrocarbon group, or a monovalent aromatic hydrocarbon group, and $R^5$ is optionally bonded to $R^6$ to form a second alicyclic structure together with the carbon atom bonded to $R^5$, with the carbon atom bonded to $R^3$ and with the carbon atom bonded to $R^6$; $R^6$ is a monovalent chain hydrocarbon group; $R^6$ is bonded to $R^3$ to form the first alicyclic structure together with the carbon atom bonded to $R^6$ and with the carbon atom bonded to $R^3$, or $R^6$ is bonded to $R^5$ to form the second alicyclic structure together with the carbon atom bonded to $R^6$, with the carbon atom bonded to $R^3$ and with the carbon atom bonded to $R^5$; and at least one hydrogen atom of $R^2$, $R^3$, or $R^4$ is optionally substituted with a fluorine atom. In a case where $R^6$ and $R^5$ are bonded to each other to form the second alicyclic structure, $R^2$ is a hydrogen atom; $R^3$ is a hydrogen atom, a monovalent chain hydrocarbon group, a monovalent alicyclic hydrocarbon group, or a monovalent aromatic hydrocarbon group; optionally, $R^3$ and $R^4$ are bonded to each other to form an alicyclic structure or an aromatic heterocyclic structure together with the carbon atom bonded to $R^3$ and with the carbon atom bonded to $R^4$, or $R^4$ and $R^5$ are bonded to each other to form an alicyclic structure or an aromatic heterocyclic structure together with the carbon atom bonded to $R^4$ and with the carbon atom bonded to $R^5$; and X is a halogen atom, a hydroxyl group, or $R^ZCOO-$, wherein $R^Z$ is a monovalent hydrocarbon group.

DESCRIPTION OF THE EMBODIMENTS

According to one embodiment of the invention, a radiation-sensitive resin composition includes [A] a polymer that includes a structural unit represented by the following formula (1) (hereinafter may be referred to as "structural unit (I)") (hereinafter may be referred to as "polymer [A]"), and [B] an acid generator (hereinafter may be referred to as "acid generator [B]").

wherein $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, and $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, and $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom.

When the polymer [A] includes the structural unit (I) that includes the above specific structure, the PEB temperature can be reduced, and a resist pattern can be formed with more excellent sensitivity, LWR performance, and resolution. The reason why the radiation-sensitive resin composition that has the above configuration achieves the above advantageous effects is not necessarily clear. It is conjectured that the acid-labile group included in the structural unit (I) exhibits a high dissociation capability since the acid-labile group has an alicyclic structure, and the carbon atom bonded to the ester group is situated at the allylic position with respect to the carbon-carbon double bond, for example.

The structural unit (I) is preferably represented by the following formula (1-1).

(1-1)

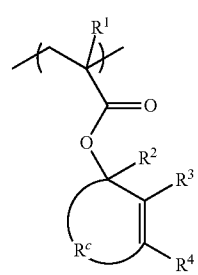

wherein $R^1$ is the same as defined for the formula (1), $R^2$ is a hydrogen atom, $R^3$ is a hydrogen atom, a monovalent chain hydrocarbon group, a monovalent alicyclic hydrocarbon group, or a monovalent aromatic hydrocarbon group, $R^C$ is an organic group necessary for forming an alicyclic structure together with the carbon atoms respectively bonded to $R^2$, $R^3$, and $R^4$, and $R^4$ is a hydrogen atom, a monovalent chain hydrocarbon group, a monovalent alicyclic hydrocarbon group, or a monovalent aromatic hydrocarbon group, or is bonded to at least one carbon atom included in $R^3$ or $R^C$ to form an alicyclic structure or an aromatic heterocyclic structure.

When the polymer [A] includes the specific structural unit (I) represented by the formula (1-1), the PEB temperature can be further reduced, and a resist pattern can be formed with more excellent sensitivity, LWR performance, and resolution. The structural unit (I) exhibits an improved acid dissociation capability when a carbon-carbon double bond is included in the ring of the alicyclic structure. As a result, the PEB temperature can be further reduced, and a resist pattern can be formed with more excellent sensitivity, LWR performance, and resolution.

It is also preferable that the structural unit (I) be represented by the following formula (1-2).

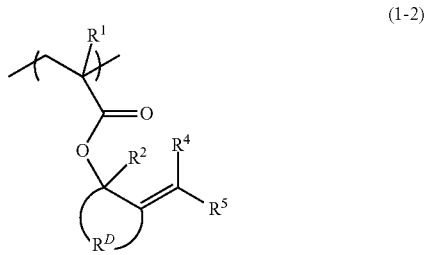

(1-2)

wherein $R^1$, $R^2$, and $R^4$ are the same as defined for the formula (1), $R^5$ is a hydrogen atom, a monovalent chain hydrocarbon group, a monovalent alicyclic hydrocarbon group, or a monovalent aromatic hydrocarbon group, and $R^D$ is an organic group necessary for forming an alicyclic structure together with the carbon atom bonded to $R^2$, and the carbon atom that is adjacent to the carbon atom bonded to $R^2$, and forms a carbon-carbon double bond.

When the polymer [A] includes the specific structural unit (I) represented by the formula (1-2), the PEB temperature can be reduced, and a resist pattern can be formed with excellent sensitivity, LWR performance, and resolution. The structural unit (I) exhibits an excellent acid dissociation capability even when a carbon-carbon double bond is not included in the ring of the alicyclic structure. As a result, the PEB temperature can be further reduced, and a resist pattern can be formed with more excellent sensitivity, LWR performance, and resolution.

$R^2$ in the formula (1-2) may preferably be a hydrogen atom. When $R^2$ is a hydrogen atom, the PEB temperature can be reduced, and a resist pattern can be formed with excellent sensitivity, LWR performance, and resolution. A compound that produces such a structural unit can be easily synthesized using a cyclic α,β-unsaturated ketone and a hydrogenation agent.

The hydrocarbon group represented by $R^2$ in the formula (1) is preferably a chain hydrocarbon group or an alicyclic hydrocarbon group. When $R^2$ is the above specific group, the PEB temperature can be further reduced, and a resist pattern can be formed with more excellent sensitivity, LWR performance, and resolution.

The alicyclic structure formed by $R^3$ and $R^6$ in the formula (1) together with the carbon atoms respectively bonded to $R^3$ and $R^6$, or the alicyclic structure formed by $R^5$ and $R^6$ in the formula (1) together with the carbon atoms respectively bonded to $R^5$ and $R^6$, is preferably an alicyclic hydrocarbon structure. When the polymer [A] includes the structural unit (I) that includes such a specific alicyclic structure, the PEB temperature can be further reduced, and a resist pattern can be formed with more excellent sensitivity, LWR performance, and resolution.

It is preferable that at least one group selected from the group consisting of —CO—, —COO—, —O—, —NR— (wherein R is a hydrogen atom or a monovalent hydrocarbon group), —CS—, —S—, —SO—, and —SO$_2$— be present between carbon atoms included in the alicyclic structure formed by $R^3$ and $R^6$ in the formula (1) together with the carbon atoms respectively bonded to $R^3$ and $R^6$, or the alicyclic structure formed by $R^5$ and $R^6$ in the formula (1) together with the carbon atoms respectively bonded to $R^5$ and $R^6$. When the polymer [A] includes the structural unit (I) that includes such a specific structure, the PEB temperature can be further reduced, and a resist pattern can be formed with more excellent sensitivity, LWR performance, and resolution.

It is preferable that $R^3$ and $R^4$ in the formula (1) be independently a hydrogen atom, a monovalent chain hydrocarbon group, or a monovalent alicyclic hydrocarbon group. When $R^3$ and $R^4$ in the formula (1) are independently a hydrogen atom, a monovalent chain hydrocarbon group, or a monovalent alicyclic hydrocarbon group, the PEB temperature can be further reduced, and a resist pattern can be formed with more excellent sensitivity, LWR performance, and resolution.

According to another embodiment of the invention, a resist pattern-forming method includes forming a resist film on a substrate using the radiation-sensitive resin composition; exposing the resist film; heating the exposed resist film; and developing the heated resist film.

According to the resist pattern-forming method, the PEB temperature can be reduced, and a resist pattern can be formed with excellent sensitivity, LWR performance, and resolution.

It is preferable to heat the exposed resist film at 90° C. or less. In this case, a resist pattern can be formed with more excellent sensitivity, LWR performance, and resolution.

According to another embodiment of the invention, a polymer includes the structural unit (I) represented by the following formula (1).

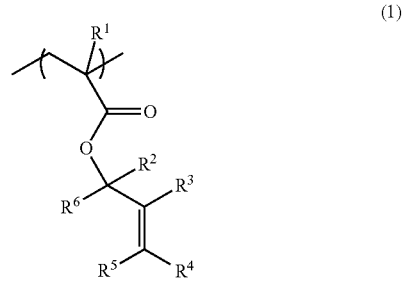

(1)

wherein $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, and $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom.

Since the polymer includes the structural unit (I) represented by the formula (1), the polymer may suitably be used as a component of the radiation-sensitive resin composition. The radiation-sensitive resin composition that includes the polymer makes it possible to reduce the PEB temperature, and can form a resist pattern with excellent sensitivity, LWR performance, and resolution.

According to another embodiment of the invention, a compound is represented by the following formula (i) (hereinafter may be referred to as "compound (i)").

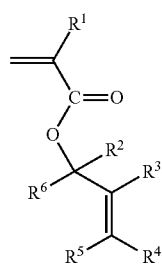

(i)

wherein $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, and $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom.

Since the compound has the structure represented by the formula (i), the compound may suitably be used as a monomer compound for incorporating the structural unit (I) in a polymer.

According to another embodiment of the invention, a method for producing a compound represented by the following formula (i) includes: reacting a cyclic α,β-unsaturated ketone represented by the following formula (a) with an organolithium compound represented by the following formula (b) or a hydrogenation agent to obtain a cyclic unsaturated alcohol represented by the following formula (c); and reacting the cyclic unsaturated alcohol represented by the formula (c) with a compound represented by the following formula (d)

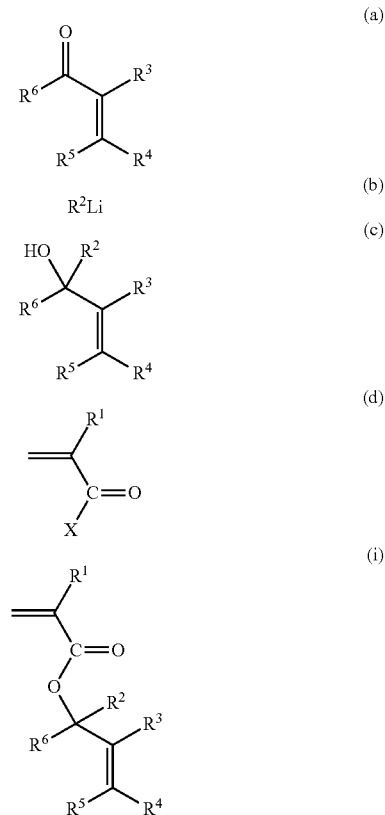

wherein $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom, X is a halogen atom, a hydroxyl group, or $R^ZCOO$—, and $R^Z$ is a monovalent hydrocarbon group.

The compound (i) can be easily synthesized by the above method.

The term "chain hydrocarbon group" used herein refers to a hydrocarbon group that does not include a cyclic structure, but includes only a chain structure. The term "chain hydrocarbon group" used herein includes a linear hydrocarbon group and a branched hydrocarbon group. The term "alicyclic structure" used herein refers to a cyclic structure that excludes an aromatic ring, and includes only carbon atoms as the ring atoms, or includes carbon atoms and a heteroatom (e.g., oxygen atom, nitrogen atom, or sulfur atom) as the ring atoms. The term "organic group" used herein refers to a group that includes at least one carbon atom.

The embodiments of the invention thus provide a radiation-sensitive resin composition that makes it possible to reduce the PEB temperature, and can form a resist pattern with excellent sensitivity, LWR performance, and resolution, a polymer that may suitably be used as a component of the radiation-sensitive resin composition, a compound that may suitably be used for the polymer, and a method for producing the compound. Therefore, the radiation-sensitive resin composition and the like may suitably be used for lithography that will be required to achieve a further reduction in line width. The embodiments will now be described in detail.

Radiation-Sensitive Resin Composition

A radiation-sensitive resin composition according to one embodiment of the invention includes the polymer [A] and the acid generator [B]. The radiation-sensitive resin composition may include [C] a solvent and [D] an acid diffusion controller as preferable components. The radiation-sensitive resin composition may further include [E] an additional polymer and an additional optional component as long as the advantageous effects of the invention are not impaired. Each component is described in detail below.

Polymer [A]

The polymer [A] includes the structural unit (I) represented by the formula (1). The polymer [A] serves as (1) a base polymer or (2) a water-repellent additive in a resist film formed using the radiation-sensitive resin composition. The base polymer (1) is a polymer that serves as the main component of a resist film formed using the radiation-sensitive resin composition. The water-repellent additive (2) is a polymer that is incorporated in the radiation-sensitive resin composition when applying the radiation-sensitive resin composition to liquid immersion lithography, and tends to be unevenly distributed in the surface area of the resulting resist film. A polymer that exhibits high hydrophobicity as compared with a polymer that is used as the base polymer tends to be unevenly distributed in the surface area of the resulting resist film, and functions as the water-repellent additive. When the radiation-sensitive resin composition includes the water-repellent additive, elution of the acid generator and the like from the resulting resist film can be suppressed. Moreover, since the surface of the resulting resist film shows a large dynamic contact angle with water, the surface of the resist film exhibits an excellent draining capability. Therefore, high-speed scan exposure can be implemented during liquid immersion lithography while suppressing occurrence of defects (e.g., watermark defects) without additionally forming an upper layer film that isolates the surface of the resist film from an immersion medium.

When the radiation-sensitive resin composition includes both the base polymer and the water-repellent additive, the advantageous effects of the invention can be sufficiently achieved even when the polymer [A] is used as either the base polymer or the water-repellent additive. It is preferable to use the polymer [A] as both the base polymer and the water-repellent additive in order to further improve the sensitivity, the LWR performance, and the resolution when forming a resist pattern.

Structural Unit (I)

The structural unit (I) is represented by the formula (1). The acid-labile group included in the structural unit (I) exhibits a very high dissociation capability. Therefore, the PEB temperature can be reduced when using the radiation-sensitive resin composition. As a result, the acid diffusion length can be optimized, and a resist pattern can be formed with excellent sensitivity, LWR performance, and resolution. The reason why the acid-labile group included in the structural unit (I) exhibits a high dissociation capability is not necessarily clear. It is conjectured that the acid-labile group included in the structural unit (I) exhibits a high dissociation capability since the acid-labile group has an alicyclic structure, and the carbon atom bonded to the ester group is situated at the allylic position with respect to the carbon-carbon double bond, for example.

In the formula (1), $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom.

The monovalent hydrocarbon group represented by $R^2$ is preferably a monovalent chain hydrocarbon group, a monovalent alicyclic hydrocarbon group, or the like. When $R^2$ is the above specific group, the PEB temperature can be further reduced, and a resist pattern can be formed with more excellent sensitivity, LWR performance, and resolution.

Examples of the chain hydrocarbon group include chain saturated hydrocarbon groups such as a methyl group, an ethyl group, an i-propyl group, an n-propyl group, an i-butyl group, a sec-butyl group, a t-butyl group, an n-butyl group, an n-pentyl group, an n-hexyl group, an n-heptyl group, an n-octyl group, and an n-decyl group; chain unsaturated hydrocarbon groups such as an ethenyl group, a propynyl group, and an ethynyl group; and the like. Among these, chain hydrocarbon groups having 1 to 6 carbon atoms are preferable, and chain saturated hydrocarbon groups having 1 to 6 carbon atoms are more preferable.

Examples of the alicyclic hydrocarbon group include alicyclic saturated hydrocarbon groups such as a cyclobutyl group, a cyclopentyl group, a cyclohexyl group, a cyclooctyl group, and an adamantyl group; alicyclic unsaturated hydrocarbon groups such as a cyclobutenyl group and a cyclopentenyl group; and the like. Among these, alicyclic saturated hydrocarbon groups having 4 to 8 carbon atoms are preferable.

The monovalent hydrocarbon group represented by $R^2$ is preferably a chain hydrocarbon group, and more preferably a methyl group, an ethyl group, or an i-propyl group.

$R^2$ is a hydrogen atom when $R^6$ and $R^5$ are bonded to each other. $R^2$ is preferably a hydrogen atom when $R^6$ and $R^3$ are bonded to each other. When $R^2$ is a hydrogen atom, the PEB temperature can be reduced, and a resist pattern can be formed with excellent sensitivity, LWR performance, and resolution. A compound that produces such a structural unit can be easily synthesized using a cyclic α,β-unsaturated ketone and a hydrogenation agent.

Examples of the monovalent chain hydrocarbon group represented by $R^3$, $R^4$, and $R^5$ include those mentioned above in connection with the monovalent chain hydrocarbon group represented by $R^2$, and the like.

Examples of the monovalent alicyclic hydrocarbon group represented by $R^3$, $R^4$, and $R^5$ include those mentioned above in connection with the monovalent alicyclic hydrocarbon group represented by $R^2$, and the like.

Examples of the monovalent aromatic hydrocarbon group represented by $R^3$, $R^4$, and $R^5$ include a phenyl group, a naphthyl group, a phenanthryl group, an anthranyl group, a fluorenyl group, groups obtained by substituting some or all of the hydrogen atoms of these groups with a substituent, and the like. Among these, aromatic hydrocarbon groups having 6 to 15 carbon atoms are preferable, and aromatic hydrocarbon groups having 6 to 10 carbon atoms are more preferable.

$R^3$ and $R^4$ are preferably a hydrogen atom, a monovalent chain hydrocarbon group, or a monovalent alicyclic hydrocarbon group. When $R^3$ and $R^4$ in the formula (1) are a hydrogen atom, a monovalent chain hydrocarbon group, or a monovalent alicyclic hydrocarbon group, the PEB temperature can be further reduced, and a resist pattern can be formed with more excellent sensitivity, LWR performance, and resolution. $R^3$ and $R^4$ are more preferably a hydrogen atom or a monovalent chain hydrocarbon group.

Examples of the alicyclic structure formed by $R^3$ and $R^6$ together with the carbon atoms respectively bonded to $R^3$ and $R^6$ include an aliphatic heterocyclic structure and an alicyclic hydrocarbon structure.

It is preferable that the aliphatic heterocyclic structure have a structure in which at least one group selected from the group consisting of —CO—, —COO—, —O—, —NR— (wherein R is a hydrogen atom or a monovalent hydrocarbon group), —CS—, —S—, —SO—, and —SO$_2$— is present between carbon atoms included in the alicyclic structure. Examples of the monovalent hydrocarbon group represented by R include those mentioned above in connection with the monovalent hydrocarbon group represented by $R^2$, and the like. When the polymer [A] includes the structural unit (I) that includes such a specific alicyclic structure, the PEB temperature can be further reduced, and a resist pattern can be formed with more excellent sensitivity, LWR performance, and resolution.

Examples of the alicyclic hydrocarbon structure include a cyclobutane structure, a cyclopentane structure, a cyclohexane structure, a cycloheptane structure, a cyclooctane structure, and the like. Among these, a cyclopentane structure and a cyclohexane structure are preferable. Some or all of the hydrogen atoms of the alicyclic structure may be substituted with a substituent. The substituent is preferably a chain hydrocarbon group, more preferably an alkyl group, an alkenyl group, or a hydroxyl group-containing alkyl group, and still more preferably a methyl group, a propenyl group, or a 2-hydroxy-2-propyl group. When the polymer [A] includes the structural unit (I) that includes such a specific alicyclic structure, the PEB temperature can be further reduced, and a resist pattern can be formed with more excellent sensitivity, LWR performance, and resolution.

Examples of the alicyclic structure formed by $R^5$ and $R^6$ together with the carbon atoms respectively bonded to $R^5$ and $R^6$ include an aliphatic heterocyclic structure and an alicyclic hydrocarbon structure.

It is preferable that the aliphatic heterocyclic structure have a structure in which at least one group selected from the group consisting of —CO—, —COO—, —O—, —NR— (wherein R is a hydrogen atom or a monovalent hydrocarbon group), —CS—, —S—, —SO—, and —SO$_2$— is present between carbon atoms included in the alicyclic structure. Examples of the monovalent hydrocarbon group represented by R include those mentioned above in connection with the monovalent hydrocarbon group represented by $R^2$, and the like. When the polymer [A] includes the structural unit (I) that includes such a specific alicyclic structure, the PEB temperature can be further reduced, and a resist pattern can be formed with more excellent sensitivity, LWR performance, and resolution.

Examples of the alicyclic hydrocarbon structure include a cyclobutene structure, a cyclopentene structure, a cyclohexene structure, a cycloheptene structure, a cyclooctene structure, structures obtained by substituting some or all of the hydrogen atoms of these cyclic structures with a substituent, and the like. Among these, a cyclopentene structure, a cyclohexene structure, and structures obtained by substituting some or all of the hydrogen atoms of these cyclic structures with a substituent are preferable. The substituent is preferably a chain hydrocarbon group, more preferably an alkyl group, an alkenyl group, or a hydroxyl group-containing alkyl group, and still more preferably a methyl group, a propenyl group, or a 2-hydroxy-2-propyl group. When the polymer [A] includes the structural unit (I) that includes such a specific alicyclic structure, the PEB temperature can be further reduced, and a resist pattern can be formed with more excellent sensitivity, LWR performance, and resolution.

Examples of the alicyclic structure formed by $R^3$ and $R^4$ together with the carbon atoms respectively bonded to $R^3$ and $R^4$ when $R^5$ and $R^6$ are bonded to each other include alicyclic hydrocarbon structures such as a cyclopropene structure, a cyclobutene structure, a cyclopentene structure, a cyclohexene structure, and a norbornene structure, and aliphatic heterocyclic structures such as a thiacyclopentane structure, an oxacyclopentane structure, and an azacyclopentane structure.

Examples of the aromatic heterocyclic structure formed by $R^3$ and $R^4$ together with the carbon atoms respectively bonded to $R^3$ and $R^4$ when $R^5$ and $R^6$ are bonded to each other include a thiophene structure, a furan structure, a pyrrole structure, and the like. Among these, a thiophene structure and a furan structure are preferable.

Examples of the alicyclic structure formed by $R^4$ and $R^5$ together with the carbon atom bonded to $R^4$ and $R^5$ when $R^5$ and $R^6$ are bonded to each other include alicyclic hydrocarbon structures such as a cyclopropane structure, a cyclobutane structure, a cyclopentane structure, a cyclohexane structure, and a norbornane structure. Among these, a cyclopentane structure and a cyclohexane structure are preferable.

The structural unit (I) is preferably represented by the following formula (1-1).

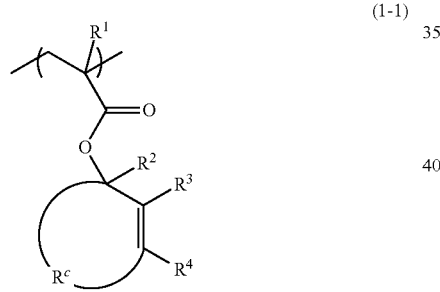

(1-1)

wherein $R^1$ is the same as defined for the formula (1), $R^2$ is a hydrogen atom, $R^3$ is a hydrogen atom, a monovalent chain hydrocarbon group, a monovalent alicyclic hydrocarbon group, or a monovalent aromatic hydrocarbon group, $R^C$ is an organic group necessary for forming an alicyclic structure together with the carbon atoms respectively bonded to $R^2$, $R^3$, and $R^4$, and $R^4$ is a hydrogen atom, a monovalent chain hydrocarbon group, a monovalent alicyclic hydrocarbon group, or a monovalent aromatic hydrocarbon group, or is bonded to at least one carbon atom included in $R^3$ or $R^C$ to form an alicyclic structure or an aromatic heterocyclic structure.

When the polymer [A] includes the specific structural unit (I) represented by the formula (1-1), the PEB temperature can be further reduced, and a resist pattern can be formed with more excellent sensitivity, LWR performance, and resolution. The structural unit (I) exhibits an improved acid dissociation capability when a carbon-carbon double bond is included in the ring of the alicyclic structure. As a result, the PEB temperature can be further reduced, and a resist pattern can be formed with more excellent sensitivity, LWR performance, and resolution.

Examples of the alicyclic structure formed by $R^C$ together with the carbon atoms respectively bonded to $R^2$, $R^3$, and $R^4$ include an aliphatic heterocyclic structure and an alicyclic hydrocarbon structure.

Examples of the aliphatic heterocyclic structure and the alicyclic hydrocarbon structure include those mentioned above in connection with the alicyclic structure formed by $R^5$ and $R^6$ in the formula (1) together with the carbon atoms respectively bonded to $R^5$ and $R^6$, and the like.

Examples of the alicyclic structure formed by $R^3$ and $R^4$ in the formula (1-1) include alicyclic hydrocarbon structures such as a cyclopropene structure, a cyclobutene structure, a cyclopentene structure, a cyclohexene structure, and a norbornene structure, and aliphatic heterocyclic structures such as a thiacyclopentane structure, an oxacyclopentane structure, and an azacyclopentane structure.

Examples of the aromatic heterocyclic structure formed by $R^3$ and $R^4$ in the formula (1-1) include a thiophene structure, a furan structure, a pyrrole structure, and the like. Among these, a thiophene structure and a furan structure are preferable.

Examples of the alicyclic structure formed by $R^4$ together with at least one carbon atom included in $R^C$ include those mentioned above in connection with the alicyclic structure formed by $R^4$ and $R^5$ in the formula (1) together with the carbon atom bonded to $R^4$ and $R^5$ when $R^5$ and $R^6$ are bonded to each other, and the like. Among these, a cyclopentane structure and a cyclohexane structure are preferable.

Examples of the structural unit (I) represented by the formula (1-1) include structural units respectively represented by the following formulas (1-1-1) to (1-1-18) (hereinafter may be referred to as "structural units (1-1-1) to (1-1-18)").

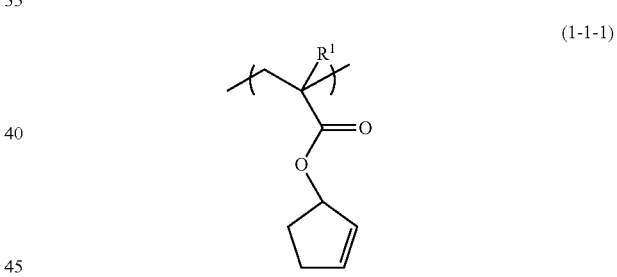

(1-1-1)

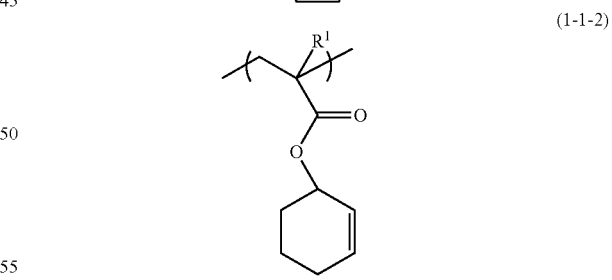

(1-1-2)

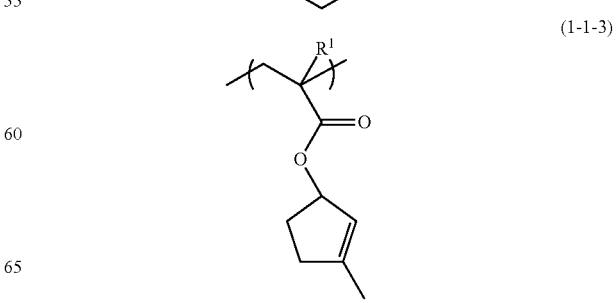

(1-1-3)

-continued
(1-1-4)
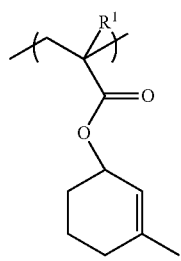
(1-1-5)
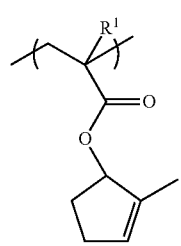
(1-1-6)
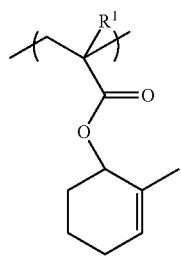
(1-1-7)
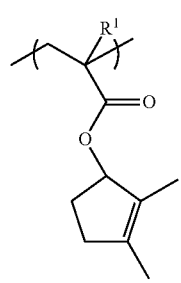
(1-1-8)
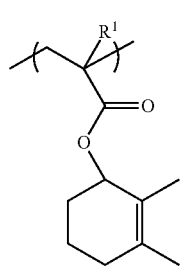
(1-1-9)
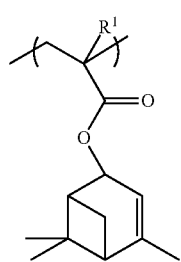
-continued
(1-1-10)
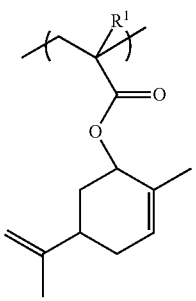
(1-1-11)
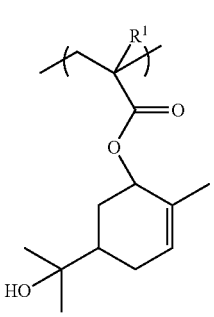
(1-1-12)
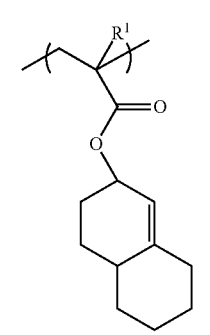
(1-1-13)
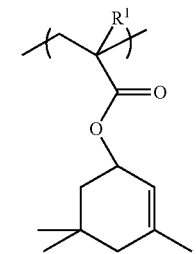
(1-1-14)
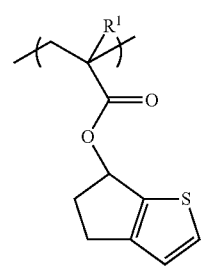

(1-1-15)

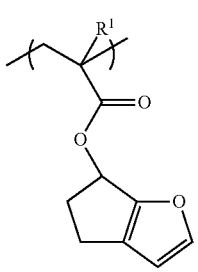

(1-1-16)

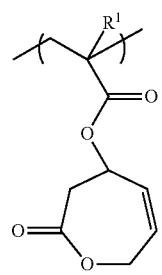

(1-1-17)

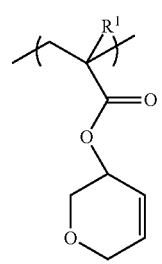

(1-1-18)

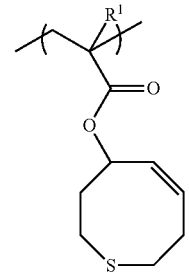

wherein $R^1$ is the same as defined for the formula (1).

Among these, the structural units (1-1-1) to (1-1-15) are preferable.

It is also preferable that the structural unit (I) be represented by the following formula (1-2).

(1-2)

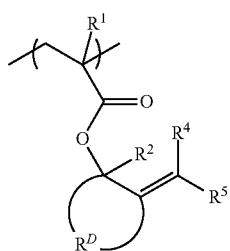

wherein $R^1$, $R^2$, and $R^4$ are the same as defined for the formula (1), $R^5$ is a hydrogen atom, a monovalent chain hydrocarbon group, a monovalent alicyclic hydrocarbon group, or a monovalent aromatic hydrocarbon group, and $R^D$ is an organic group necessary for forming an alicyclic structure together with the carbon atom bonded to $R^2$, and the carbon atom that is adjacent to the carbon atom bonded to $R^2$, and forms a carbon-carbon double bond.

When the polymer [A] includes the specific structural unit (I) represented by the formula (1-2), the PEB temperature can be reduced, and a resist pattern can be formed with excellent sensitivity, LWR performance, and resolution. The structural unit (I) exhibits an excellent acid dissociation capability even when a carbon-carbon double bond is not included in the ring of the alicyclic structure. As a result, the PEB temperature can be further reduced, and a resist pattern can be formed with more excellent sensitivity, LWR performance, and resolution.

$R^2$ in the formula (1-2) is preferably a hydrogen atom or a chain hydrocarbon group, and more preferably a hydrogen atom, a methyl group, an ethyl group, or an i-propyl group. When $R^2$ is a hydrogen atom, the PEB temperature can be reduced, and a resist pattern can be formed with excellent sensitivity, LWR performance, and resolution. A compound that produces such a structural unit can be easily synthesized using a cyclic $\alpha,\beta$-unsaturated ketone and a hydrogenation agent.

$R^4$ and $R^5$ in the formula (1-2) are preferably a hydrogen atom or a methyl group. It is more preferable that both $R^4$ and $R^5$ be a hydrogen atom or a methyl group.

Examples of the alicyclic structure formed by $R^D$ together with the carbon atom bonded to $R^2$, and the carbon atom that is adjacent to the carbon atom bonded to $R^2$, and forms a carbon-carbon double bond, include an aliphatic heterocyclic structure and an alicyclic hydrocarbon structure.

Examples of the aliphatic heterocyclic structure and the alicyclic hydrocarbon structure include those mentioned above in connection with the alicyclic structure formed by $R^3$ and $R^6$ in the formula (1) together with the carbon atoms respectively bonded to $R^3$ and $R^6$, and the like.

Examples of the alicyclic hydrocarbon structure include a cyclobutene structure, a cyclopentene structure, a cyclohexene structure, a cycloheptene structure, a cyclooctene structure, and the like. Among these, a cyclopentene structure and a cyclohexene structure are preferable. When the polymer [A] includes the structural unit (I) that includes such a specific alicyclic structure, the PEB temperature can be further reduced, and a resist pattern can be formed with more excellent sensitivity, LWR performance, and resolution.

Examples of the structural unit (I) represented by the formula (1-2) include structural units respectively represented by the following formulas (1-2-1) to (1-2-12) (hereinafter may be referred to as "structural units (1-2-1) to (1-2-12)").

(1-2-1)

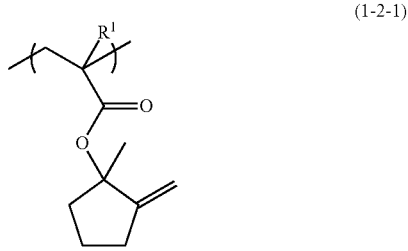

-continued
(1-2-2)
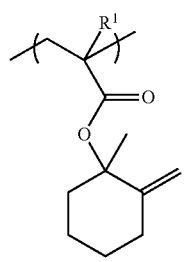
(1-2-3)
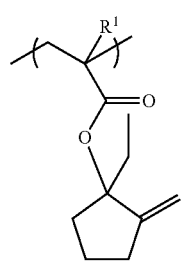
(1-2-4)
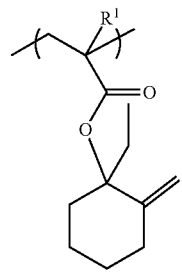
(1-2-5)
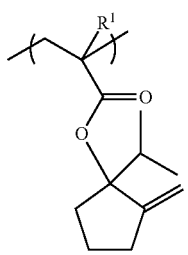
(1-2-6)
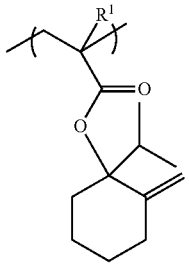
(1-2-7)
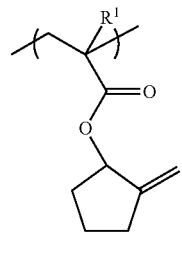
-continued
(1-2-8)
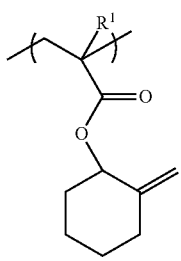
(1-2-9)
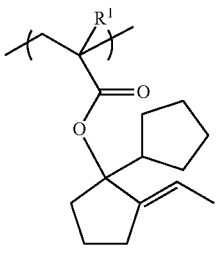
(1-2-10)
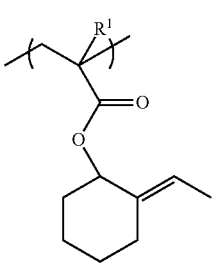
(1-2-11)
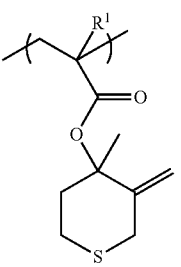
(1-2-12)
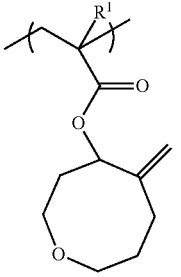
(1-2-13)
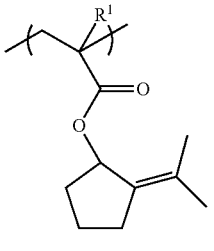

-continued (1-2-14)

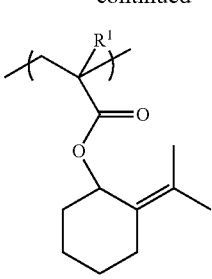

Among these, the structural units (I-2-1) to (I-2-8), (I-2-13), and (I-2-14) are preferable.

The content of the structural unit (I) in the polymer [A] is preferably 10 to 80 mol %, more preferably 20 to 70 mol %, and still more preferably 30 to 60 mol %, based on the total structural units included in the polymer [A]. When the content of the structural unit (I) is within the above range, a resist pattern can be formed with more excellent sensitivity, LWR performance, and resolution.

A monomer compound (i) that produces the structural unit (I) may be synthesized according to the following scheme, for example.

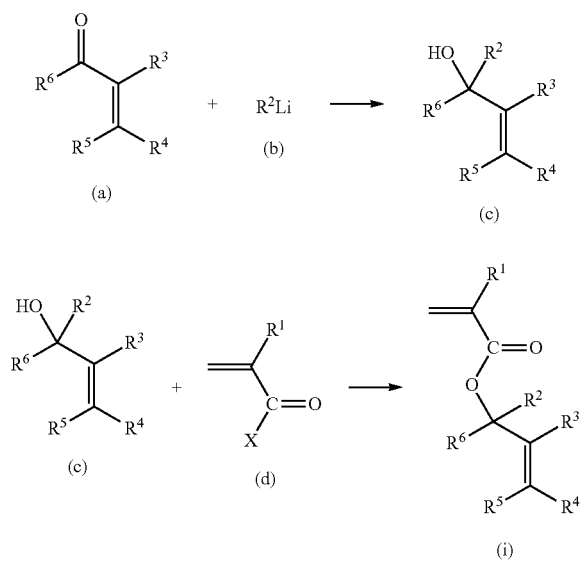

In the above scheme, $R^1$ is a hydrogen atom, a fluorine atom, a methyl group, or a trifluoromethyl group, $R^2$ is a hydrogen atom or a monovalent hydrocarbon group, $R^3$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^3$ and $R^6$, $R^4$ is a hydrogen atom, a monovalent chain hydrocarbon group, a monovalent alicyclic hydrocarbon group, or a monovalent aromatic hydrocarbon group, $R^5$ is a hydrogen atom, a monovalent chain hydrocarbon group, a monovalent alicyclic hydrocarbon group, or a monovalent aromatic hydrocarbon group, or is bonded to $R^6$ to form an alicyclic structure together with the carbon atoms respectively bonded to $R^5$ and $R^6$, $R^6$ is a monovalent chain hydrocarbon group, and is bonded to $R^3$ or $R^5$ to form an alicyclic structure together with the carbon atoms respectively bonded to $R^3$ or $R^5$ and $R^6$, provided that, when $R^6$ and $R^5$ are bonded to each other, $R^2$ is a hydrogen atom, and $R^3$ and $R^4$ are independently a hydrogen atom, a monovalent chain hydrocarbon group, a monovalent alicyclic hydrocarbon group, or a monovalent aromatic hydrocarbon group, or $R^3$ and $R^4$ are bonded to each other to form an alicyclic structure or an aromatic heterocyclic structure together with the carbon atoms respectively bonded to $R^3$ and $R^4$, or $R^4$ and $R^5$ are bonded to each other to form an alicyclic structure or an aromatic heterocyclic structure together with the carbon atom bonded to $R^4$ and $R^5$, and some or all of the hydrogen atoms of $R^2$, $R^3$, and $R^4$ are optionally substituted with a fluorine atom, X is a halogen atom, a hydroxyl group, or $R^ZCOO$—, and $R^Z$ is a monovalent hydrocarbon group.

The cyclic α,β-unsaturated ketone is reacted with the organolithium compound or the hydrogenation agent (e.g., LiAlH$_4$) in a solvent (e.g., tetrahydrofuran (THF)) to obtain the cyclic unsaturated alcohol compound. A (meth)acryloyl halide, (meth)acrylic acid, or (meth)acrylic anhydride is reacted with the unsaturated alcohol compound in the presence of a base (e.g., organic amine) to synthesize the compound (i).

Examples of the halogen atom represented by X include a chlorine atom, a bromine atom, and an iodine atom. Among these, a chlorine atom is preferable.

Examples of the monovalent chain hydrocarbon group represented by $R^Z$ include those mentioned above in connection with the monovalent chain hydrocarbon group represented by $R^3$, $R^4$, and $R^5$, and the like.

Examples of the monovalent aromatic hydrocarbon group represented by $R^Z$ include those mentioned above in connection with the monovalent aromatic hydrocarbon group represented by $R^3$, $R^4$, and $R^5$, and the like.

The polymer [A] may include the following structural units (II) to (VII) and an additional structural unit in addition to the structural unit (I). Note that the polymer [A] may include two or more types of each structural unit. Each structural unit is described in detail below.

Structural Unit (II)

The structural unit (II) is a structural unit represented by the following formula (2). When the polymer [A] is used as the base polymer, the hydrophilicity of the resulting resist film can be appropriately adjusted by incorporating the structural unit (II) in the polymer [A]. When the polymer [A] is used as the water-repellent additive, an improvement in hydrophobicity can be achieved by incorporating the structural unit (II) that includes a fluorine atom in the polymer [A], and the dynamic contact angle of the surface of a resist film formed using the resulting radiation-sensitive resin composition can be further improved.

(2)

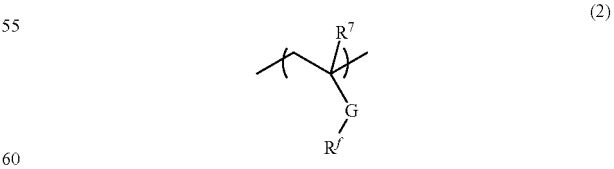

wherein $R^7$ is a hydrogen atom, a fluorine atom, a methyl group, or a trifluoromethyl group, G is a single bond, an oxygen atom, a sulfur atom, —CO—O—, —SO$_2$—O—NH—, —CO—NH—, or —O—CO—NH—, and $R^f$ is a monovalent chain hydrocarbon group having 1 to 6 carbon atoms that includes at least one fluorine atom, or a monovalent alicyclic hydrocarbon group having 4 to 20 carbon atoms that includes at least one fluorine atom.

Examples of the chain hydrocarbon group having 1 to 6 carbon atoms include a trifluoromethyl group, a 2,2,2-trifluoroethyl group, a perfluoroethyl group, 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the alicyclic hydrocarbon group having 4 to 20 carbon atoms include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of a monomer that produces the structural unit (II) include trifluoromethyl(meth)acrylate, 2,2,2-trifluoroethyl(meth)acrylate, perfluoroethyl(meth)acrylate, perfluoro-n-propyl(meth)acrylate, perfluoro-i-propyl(meth)acrylate, perfluoro-n-butyl(meth)acrylate, perfluoro-i-butyl(meth)acrylate, perfluoro-t-butyl(meth)acrylate, 2-(1,1,1,3,3,3-hexafluoropropyl)(meth)acrylate, 1-(2,2,3,3,4,4,5,5-octafluoropentyl)(meth)acrylate, perfluorocyclohexylmethyl(meth)acrylate, 1-(2,2,3,3,3-pentafluoropropyl)(meth)acrylate, monofluorocyclopentyl(meth)acrylate, difluorocyclopentyl(meth)acrylate, perfluorocyclopentyl(meth)acrylate, monofluorocyclohexyl(meth)acrylate, difluorocyclopentyl(meth)acrylate, perfluorocyclohexylmethyl(meth)acrylate, fluoronorbornyl(meth)acrylate, fluoroadamantyl(meth)acrylate, fluorobornyl(meth)acrylate, fluoroisobornyl(meth)acrylate, fluorotricyclodecyl(meth)acrylate, fluorotetracyclodecyl(meth)acrylate, and the like.

When the polymer [A] is used as the base polymer, the content of the structural unit (II) in the polymer [A] is preferably 0 to 30 mol %, and more preferably 0 to 20 mol %, based on the total structural units included in the polymer [A]. When the content of the structural unit (II) is within the above range, the hydrophilicity of the resulting resist film can be more appropriately adjusted. When the polymer [A] is used as the water-repellent additive, the content of the structural unit (II) in the polymer [A] is preferably 30 to 100 mol %, and more preferably 50 to 100 mol %, based on the total structural units included in the polymer [A]. When the content of the structural unit (II) is within the above range, the surface of the resulting resist film shows a higher dynamic contact angle during liquid immersion lithography. The polymer [A] may include only one type of the structural unit (II), or may include two or more types of the structural unit (II).

Structural Unit (III)

The polymer [A] may include the structural unit (III) represented by the following formula (3). When the polymer [A] further includes the structural unit (III), the polymer [A] exhibits improved hydrophobicity, and the dynamic contact angle of the surface of a resist film formed using the resulting radiation-sensitive resin composition can be further improved. Moreover, the hydrophilicity of the resist film can be appropriately adjusted.

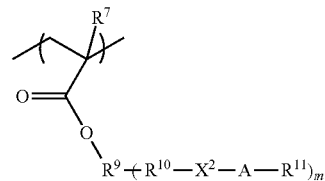

(3)

wherein $R^8$ is a hydrogen atom, a fluorine atom, a methyl group, or a trifluoromethyl group, $R^9$ is an (m+1)-valent hydrocarbon group having 1 to 20 carbon atoms, provided that an oxygen atom, a sulfur atom, —$NR^{12}$—, a carbonyl group, —CO—O—, or —CO—NH— may be bonded to the end of $R^9$ that is bonded to $R^{10}$, $R^{12}$ is a hydrogen atom or a monovalent organic group, $R^{10}$ is a single bond, a divalent chain hydrocarbon group having 1 to 10 carbon atoms, or a divalent alicyclic hydrocarbon group having 4 to 20 carbon atoms, $X^2$ is a single bond, or a divalent hydrocarbon group having 1 to 20 carbon atoms that is unsubstituted, or substituted with a fluorine atom, A is an oxygen atom, —$NR^{13}$—, —CO—O—*, or —$SO_2$—O—*, * is a bonding site bonded to $R^{11}$, $R^{13}$ is a hydrogen atom or a monovalent organic group, $R^{11}$ is a hydrogen atom or a monovalent organic group, and m is an integer from 1 to 3, provided that a plurality of $R^{10}$, a plurality of $X^2$, a plurality of A, and a plurality of $R^{11}$ are respectively either identical or different when m is 2 or 3.

When $R^{11}$ in the formula (3) is a hydrogen atom, the solubility of the polymer [A] in an alkaline developer can be improved.

Examples of the monovalent organic group represented by $R^{11}$ in the formula (3) include an acid-labile group, an alkali-labile group, and a substituted or unsubstituted hydrocarbon group having 1 to 30 carbon atoms. Examples of a substituent that may substitute the hydrocarbon group having 1 to 30 carbon atoms include —$R^{P1}$, —$R^{P2}$—O—$R^{P1}$, —$R^{P2}$—CO—$R^{P1}$, —$R^{P2}$—CO—$OR^{P1}$, —$R^{P2}$—O—CO—$R^{P1}$, —$R^{P2}$—OH, —$R^{P2}$—CN, and —$R^{P2}$—COOH (hereinafter may be collectively referred to as "$R^S$"). $R^{P1}$ is a monovalent chain saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms, provided that some or all of the hydrogen atoms of these groups are optionally substituted with a fluorine atom. $R^{P2}$ is a single bond, a divalent chain saturated hydrocarbon group having 1 to 10 carbon atoms, a divalent alicyclic saturated hydrocarbon group having 3 to 20 carbon atoms, or a divalent aromatic hydrocarbon group having 6 to 30 carbon atoms, provided that some or all of the hydrogen atoms of these groups are optionally substituted with a fluorine atom.

The term "acid-labile group" used herein refers to a group that substitutes a hydrogen atom included in a polar functional group (e.g., hydroxyl group or carboxyl group), and dissociates in the presence of an acid. The structural unit (III) thus produces a polar group due to an acid. Therefore, when $R^{11}$ is an acid-labile group, an area exposed in an exposure step included in a resist pattern-forming method described later exhibits improved solubility in an alkaline developer.

The term "alkali-labile group" used herein refers to a group that substitutes a hydrogen atom included in a polar functional group (e.g., hydroxyl group or carboxyl group), and dissociates in the presence of an alkali (e.g., in a 2.38 mass % tetramethylammonium hydroxide aqueous solution (23° C.)). The structural unit (III) thus produces a polar group due to an alkali. Therefore, when $R^{11}$ is an alkali-labile group, an improvement in solubility in an alkaline developer, and a decrease in hydrophobicity of the surface of the resist film after development can be achieved.

Examples of the acid-labile group include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, an alkoxy-substituted methyl group, an alkylsulfanyl-substituted methyl group, and the like. Examples of the alkoxy group (substituent) of the alkoxy-substituted methyl group include alkoxy groups having 1 to 4 carbon atoms, and the like. Examples of the alkyl group (substituent) of the alkylsulfanyl-substituted methyl group include alkyl groups having 1 to 4 carbon atoms, and the like. The acid-labile group may be a group represented by a formula (Y-1) described later in connection with the structural unit (IV). Among these, a t-butoxycarbonyl group and an alkoxy-substituted methyl group are preferable when A is an oxygen atom or —$NR^{13}$—. The group represented by the formula (Y-1) described later in connection with the structural unit (IV) is preferable when A is —CO—O—.

Examples of the alkali-labile group include groups respectively represented by the following formulas (W-1) to (W-5), and the like. Among these, the group represented by the formula (W-1) is preferable when A is an oxygen atom or —$NR^{13}$—. The groups respectively represented by the formulas (W-2) to (W-5) are preferable when A is —CO—O—.

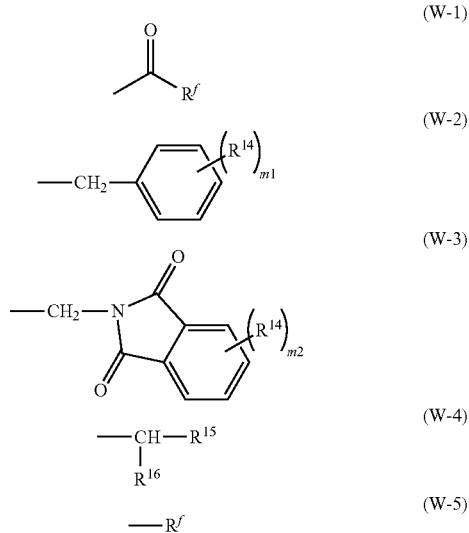

wherein $R^f$ is the same as defined for the formula (2), $R^{14}$ is a substituent, m1 is an integer from 0 to 5, m2 is an integer from 0 to 4, provided that a plurality of $R^{14}$ are either identical or different when a plurality of $R^{14}$ are present, and $R^{15}$ and $R^{16}$ are independently a hydrogen atom or an alkyl group having 1 to 10 carbon atoms, provided that $R^{15}$ and $R^{16}$ are optionally bonded to each other to form a divalent alicyclic hydrocarbon group having 4 to 20 carbon atoms together with the carbon atom bonded to $R^{15}$ and $R^{16}$.

Examples of the substituent represented by $R^{14}$ include the groups mentioned above in connection with $R^S$, and the like.

Examples of the divalent alicyclic hydrocarbon group formed by $R^{15}$ or $R^{16}$ together with the carbon atom bonded to $R^{15}$ or $R^{16}$ include a cyclopentanediyl group, a methylcyclopentanediyl group, a 2-ethylcyclopentanediyl group, a 3-ethylcyclopentanediyl group, a cyclohexanediyl group, a methylcyclohexanediyl group, a 2-ethylcyclohexanediyl group, a 3-ethylcyclohexanediyl group, a cycloheptanediyl group, a methylcycloheptanediyl group, a 2-ethylcycloheptanediyl group, a 3-ethylcycloheptanediyl group, a norbornanediyl group, and the like.

Examples of the group represented by the formula (W-4) include a methyl group, an ethyl group, a 1-propyl group, a 2-propyl group, a 1-butyl group, a 2-butyl group, a 1-pentyl group, a 2-pentyl group, a 3-pentyl group, a 1-(2-methylbutyl) group, a 1-(3-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(3-methylpentyl) group, a 2-(4-methylpentyl) group, a 3-(2-methylpentyl) group, and the like. Among these, a methyl group, an ethyl group, a 1-propyl group, a 2-propyl group, a 1-butyl group, and a 2-butyl group are preferable.

$X^2$ in the formula (3) is a divalent hydrocarbon group having 1 to 20 carbon atoms that is unsubstituted, or substituted with a fluorine atom. Examples of the divalent hydrocarbon group having 1 to 20 carbon atoms include divalent chain hydrocarbon groups having 1 to 20 carbon atoms, divalent alicyclic hydrocarbon groups having 3 to 20 carbon atoms, divalent aromatic hydrocarbon groups having 6 to 20 carbon atoms, and divalent hydrocarbon groups formed by combining groups among these groups. Some or all of the hydrogen atoms of these divalent hydrocarbon groups may be substituted with a fluorine atom.

Examples of the divalent chain hydrocarbon groups having 1 to 20 carbon atoms include chain saturated hydrocarbon groups such as a methanediyl group, an ethanediyl group, a propanediyl group, a butanediyl group, a pentanediyl group, a hexanediyl group, an octanediyl group, a decanediyl group, an undecanediyl group, a hexadecanediyl group, and an icosanediyl group; chain unsaturated hydrocarbon groups such as an ethenediyl group, a propenediyl group, a butenediyl group, a pentenediyl group, a hexenediyl group, an octenediyl group, a decenediyl group, an undecenediyl group, a hexadecenediyl group, an eicosenediyl group, an ethynediyl group, a propynediyl group, a butynediyl group, an octynediyl group, a butadieneyl group, a hexadienediyl group, and an octatrienediyl group; and the like.

Examples of the divalent alicyclic hydrocarbon groups having 3 to 20 carbon atoms include monocyclic saturated hydrocarbon groups such as a cyclopropanediyl group, a cyclobutanediyl group, a cyclopentanediyl group, a cyclohexanediyl group, a cycloheptanediyl group, a cyclooctanediyl group, a cyclodecanediyl group, a methylcyclohexanediyl group, and an ethylcyclohexanediyl group; monocyclic unsaturated hydrocarbon groups such as a cyclobutenediyl group, a cyclopentenediyl group, a cyclohexenediyl group, a cycloheptenediyl group, a cyclooctenediyl group, a cyclodecenediyl group, a cyclopentadienediyl group, a cyclohexadienediyl group, a cyclooctadienediyl group, and a cyclodecadienediyl group; polycyclic saturated hydrocarbon groups such as a bicyclo[2.2.1]heptanediyl group, a bicyclo[2.2.2]octanediyl group, a tricyclo[5.2.1.0$^{2,6}$]decanediyl group, a tricyclo[3.3.1.1$^{3,7}$]decanediyl group, a tetracyclo[6.2.1.1$^{3,6}$.0$^{2,7}$]dodecanediyl group, and an adamantanediyl group; polycyclic unsaturated hydrocarbon groups such as a bicyclo[2.2.1]heptenediyl group, a bicyclo[2.2.2]octenediyl group, a tricyclo[5.2.1.0$^{2,6}$]decenediyl group, a tricyclo[3.3.1.1$^{3,7}$]decenediyl group, and a tetracyclo[6.2.1.1$^{3,6}$.0$^{2,7}$]dodecenediyl group; and the like.

Examples of the divalent aromatic hydrocarbon groups having 6 to 30 carbon atoms include a phenylene group, a biphenylene group, a terphenylene group, a benzylene group, a phenyleneethylene group, a phenylenecyclohexylene group, a naphthylene group, and the like.

Specific examples of the divalent chain hydrocarbon group having 1 to 20 carbon atoms represented by $X^2$ include the groups respectively represented by the following formulas (X2-1) to (X2-6), and the like.

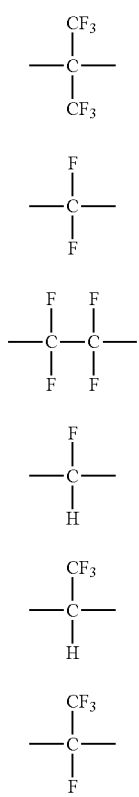

$X^2$ is preferably the group represented by the formula (X2-1) when A is an oxygen atom. $X^2$ is preferably a group among the groups respectively represented by the formulas (X2-2) to (X2-6) (more preferably the group represented by the formula (X2-2)) when A is —CO—O—.

m in the formula (3) is an integer from 1 to 3. Therefore, one, two, or three $R^{11}$ are introduced into the structural unit (III). A plurality of $R^{10}$, a plurality of $R^{11}$, a plurality of $X^2$, and a plurality of A are respectively either identical or different when m is 2 or 3. Specifically, a plurality of $R^{11}$ may have an identical structure or a different structure when m is 2 or 3. When m is 2 or 3, a plurality of $R^{10}$ may be bonded to an identical carbon atom included in $R^9$, or may be bonded to different carbon atoms included in $R^9$.

Examples of the structural unit (III) include structural units respectively represented by the following formulas (3-1a) and (3-1c), and the like.

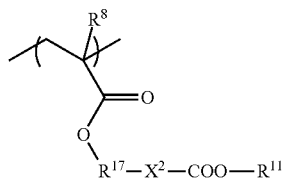
(3-1a)

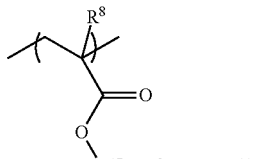
(3-1b)

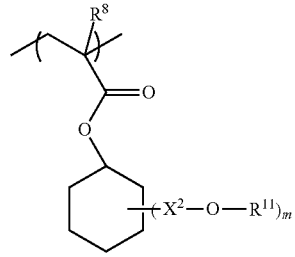
(3-1c)

wherein $R^8$, $X^2$, $R^{11}$, and m are the same as defined for the formula (3), and $R^{17}$ is a divalent linear, branched, or cyclic saturated or unsaturated hydrocarbon group having 1 to 20 carbon atoms, provided that a plurality of $X^2$ and a plurality of $R^{11}$ are respectively either identical or different when m is 2 or 3.

Examples of a monomer that produces the structural unit (III) include compounds respectively represented by the following formulas (3m-1) to (3m-15), and the like.

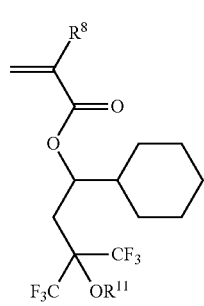
(3m-1)

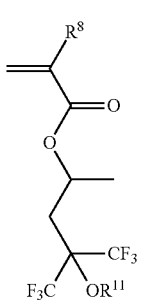
(3m-2)

-continued
(3m-3)
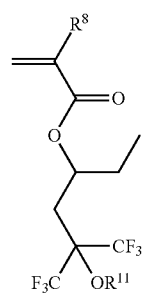
(3m-4)
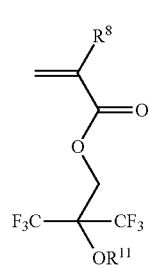
(3m-5)
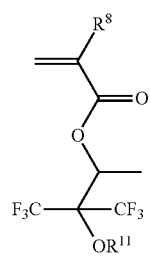
(3m-6)
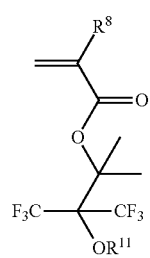
(3m-7)
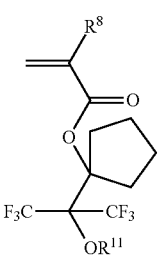
-continued
(3m-8)
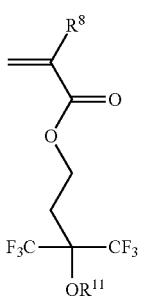
(3m-9)
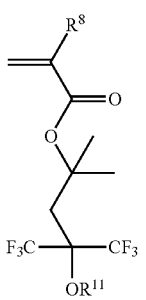
(3m-10)
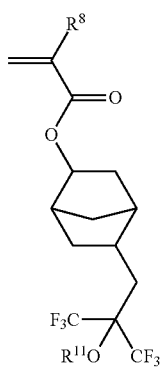
(3m-11)
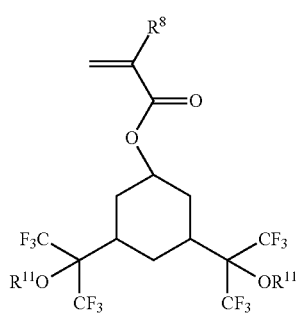
(3m-12)
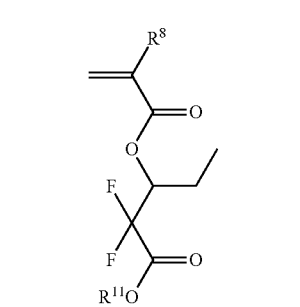

(3m-13)

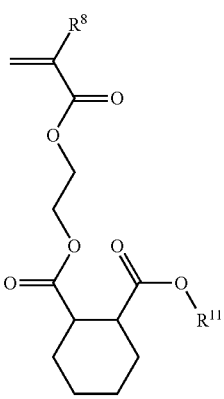

(3m-14)

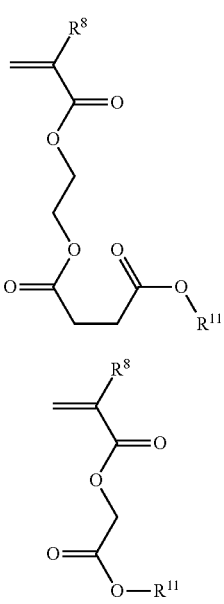

(3m-15)

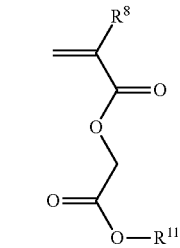

wherein $R^8$ and $R^{11}$ are the same as defined for the formula (3), provided that a plurality of $R^{11}$ are either identical or different when a plurality of $R^{11}$ are present.

When the polymer [A] is used as the base polymer, the content of the structural unit (III) in the polymer [A] is preferably 0 to 30 mol %, and more preferably 0 to 15 mol %, based on the total structural units included in the polymer [A]. When the content of the structural unit (III) is within the above range, the hydrophilicity of the resulting resist film can be more appropriately adjusted. When the polymer [A] is used as the water-repellent additive, the content of the structural unit (III) in the polymer [A] is preferably 30 to 100 mol %, and more preferably 50 to 100 mol %, based on the total structural units included in the polymer [A]. When the content of the structural unit (III) is within the above range, the surface of the resulting resist film shows a high dynamic contact angle. The polymer [A] may include only one type of the structural unit (III), or may include two or more types of the structural unit (III).

Structural Unit (IV)

The polymer [A] may include the structural unit (IV) represented by the following formula (4) that includes an acid-labile group (excluding the structural unit (I)). When the polymer [A] includes the structural unit (IV), the shape of the resulting resist pattern can be further improved.

(4)

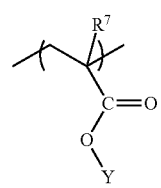

wherein $R^{18}$ is a hydrogen atom, a fluorine atom, a methyl group, or a trifluoromethyl group, and Y is an acid-labile group. Note that the structural unit (IV) excludes the structural unit (I).

The acid-labile group represented by Y is preferably a group represented by the following formula (Y-1).

(Y-1)

wherein $R^{19}$, $R^{20}$, and $R^{21}$ are independently an alkyl group having 1 to 4 carbon atoms or a monovalent alicyclic hydrocarbon group having 4 to 20 carbon atoms, provided that $R^{20}$ and $R^{21}$ are optionally bonded to each other to form a divalent alicyclic hydrocarbon group having 4 to 20 carbon atoms together with the carbon atom bonded to $R^{20}$ and $R^{21}$.

Examples of the alkyl group having 1 to 4 carbon atoms represented by $R^{19}$ to $R^{21}$ include a methyl group, an ethyl group, an n-propyl group, an i-propyl group, an n-butyl group, a 2-methylpropyl group, a 1-methylpropyl group, a t-butyl group, and the like.

Examples of the monovalent alicyclic hydrocarbon group having 4 to 20 carbon atoms represented by $R^{19}$ to $R^{21}$, and the divalent alicyclic hydrocarbon group having 4 to 20 carbon atoms formed by $R^{20}$ and $R^{21}$ together with the carbon atom bonded to $R^{20}$ and $R^{21}$, include groups having an alicyclic hydrocarbon skeleton, such as groups having a bridged skeleton (e.g., adamantane skeleton or norbornane skeleton), groups having a cycloalkane skeleton (e.g., cyclopentane skeleton or cyclohexane skeleton), and groups obtained by substituting these groups with at least one linear, branched, or cyclic alkyl group having 1 to 10 carbon atoms (e.g., methyl group, ethyl group, n-propyl group, or i-propyl group). Among these, a group having a cycloalkane skeleton is preferable since the shape of the resist pattern obtained by development can be further improved.

Examples of the structural unit (IV) include structural units respectively represented by the following formulas (4-1) to (4-4), and the like.

(4-1)

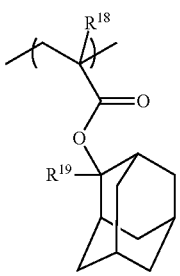

(4-2)

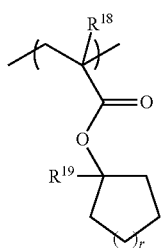

(4-3)

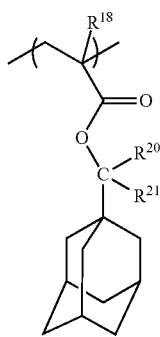

(4-4)

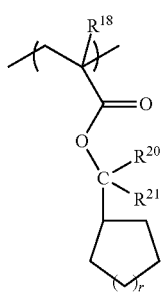

wherein $R^{18}$ is the same as defined for the formula (4), $R^{19}$ to $R^{21}$ are the same as defined for the formula (Y-1), and r is an integer from 1 to 3.

The content of the structural unit (IV) in the polymer [A] (when the polymer [A] is used as the base polymer or the water-repellent additive) is preferably 50 mol % or less, more preferably 5 to 50 mol %, and particularly preferably 10 to 40 mol %, based on the total structural units included in the polymer [A]. When the content of the structural unit (IV) is within the above range, the shape of the resulting resist pattern can be further improved. The polymer [A] may include only one type of the structural unit (IV), or may include two or more types of the structural unit (IV). The total content of the structural unit (I) and the structural unit (IV) in the polymer [A] (when the polymer [A] is used as the base polymer or the water-repellent additive) is preferably 80 mol % or less, more preferably 5 to 70 mol %, and particularly preferably 10 to 60 mol %, based on the total structural units included in the polymer [A].

Structural Unit (V)

The polymer [A] may include the structural unit (V) that includes an alkali-soluble group. When the polymer [A] includes the structural unit (V), the resulting resist film exhibits improved affinity for a developer.

The alkali-soluble group included in the structural unit (V) is preferably a functional group that includes a hydrogen atom having a pKa of 4 to 11 from the viewpoint of an improvement in solubility in a developer. Examples of such a functional group include functional groups respectively represented by the following formulas (5s-1) and (5s-2), and the like.

(5s-1)

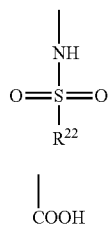

(5s-2)

|
COOH wherein $R^{22}$ is a hydrocarbon group having 1 to 10 carbon atoms that includes at least one fluorine atom.

The hydrocarbon group having 1 to 10 carbon atoms represented by $R^{22}$ that is substituted with at least one fluorine atom is not particularly limited as long as the hydrocarbon group is obtained by substituting some or all of the hydrogen atoms of a hydrocarbon group having 1 to 10 carbon atoms with a fluorine atom. Examples of the hydrocarbon group having 1 to 10 carbon atoms represented by $R^{22}$ include a trifluoromethyl group, a trifluoroethyl group, a pentafluoroethyl group, a nonafluorobutyl group, and the like. Among these, a trifluoromethyl group is preferable.

Examples of a preferable monomer that produces the structural unit (V) include, but are not limited to, methacrylic acid, a methacrylate, an acrylate, and an α-trifluoroacrylate.

Examples of the structural unit (V) include structural units respectively represented by the following formulas (5-1) and (5-2), and the like.

(5-1)

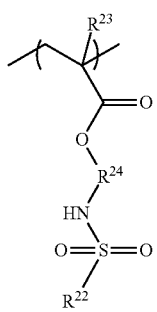

(5-2)

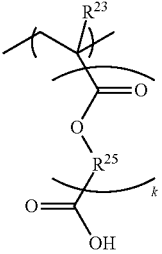

wherein $R^{23}$ is a hydrogen atom, a fluorine atom, a methyl group, or a trifluoromethyl group, $R^{22}$ is the same as defined for the formula (5s-1), $R^{24}$ is a single bond, or a divalent linear, branched, or cyclic saturated or unsaturated divalent hydrocarbon group having 1 to 20 carbon atoms, $R^{25}$ is a divalent linking group, and k is 0 or 1.

Examples of the divalent linking group represented by $R^{25}$ include divalent chain hydrocarbon groups having 1 to 30 carbon atoms, divalent alicyclic hydrocarbon groups having 3 to 30 carbon atoms, divalent aromatic hydrocarbon groups having 6 to 30 carbon atoms, groups obtained by combining these groups with an ether group, an ester group, a carbonyl group, an imino group, or an amide group, and the like. The divalent linking group may be substituted with a substituent.

Examples of the divalent chain hydrocarbon groups having 1 to 30 carbon atoms include chain saturated hydrocarbon groups such as a methanediyl group, an ethanediyl group, a propanediyl group, a butanediyl group, a pentanediyl group, a hexanediyl group, an octanediyl group, a decanediyl group, an undecanediyl group, a hexadecanediyl group, and an icosanediyl group; chain unsaturated hydrocarbon groups such as an ethenediyl group, a propenediyl group, a butenediyl group, a pentenediyl group, a hexenediyl group, an octenediyl group, a decenediyl group, an undecenediyl group, a hexadecenediyl group, an eicosenediyl group, an ethynediyl group, a propynediyl group, a butynediyl group, an octynediyl group, a butadienediyl group, a hexadienediyl group, and an octatrienediyl group; and the like.

Examples of the divalent alicyclic hydrocarbon groups having 3 to 30 carbon atoms include monocyclic saturated hydrocarbon groups such as a cyclopropanediyl group, a cyclobutanediyl group, a cyclopentanediyl group, a cyclohexanediyl group, a cycloheptanediyl group, a cyclooctanediyl group, a cyclodecanediyl group, a methylcyclohexanediyl group, and an ethylcyclohexanediyl group; monocyclic unsaturated hydrocarbon groups such as a cyclobutenediyl group, a cyclopentenediyl group, a cyclohexenediyl group, a cycloheptenediyl group, a cyclooctenediyl group, a cyclodecenediyl group, a cyclopentadienediyl group, a cyclohexadienediyl group, a cyclooctadienediyl group, and a cyclodecadienediyl group; polycyclic saturated hydrocarbon groups such as a bicyclo[2.2.1]heptanediyl group, a bicyclo[2.2.2]octanediyl group, a tricyclo[5.2.1.0$^{2,6}$]decanediyl group, a tricyclo[3.3.1.1$^{3,7}$]decanediyl group, a tetracyclo[6.2.1.1$^{3,6}$.0$^{2,7}$]dodecanediyl group, and an adamantanediyl group; polycyclic unsaturated hydrocarbon groups such as a bicyclo[2.2.1]heptenediyl group, a bicyclo[2.2.2]octenediyl group, a tricyclo[5.2.1.0$^{2,6}$]decenediyl group, a tricyclo[3.3.1.1$^{3,7}$]decenediyl group, and a tetracyclo[6.2.1.1$^{3,6}$.0$^{2,7}$]dodecenediyl group; and the like.

Examples of the divalent aromatic hydrocarbon groups having 6 to 30 carbon atoms include a phenylene group, a biphenylene group, a terphenylene group, a benzylene group, a phenyleneethylene group, a phenylenecyclohexylene group, a naphthylene group, and the like.

Further examples of the divalent linking group include groups respectively represented by the following formulas (X-1) to (X-6), and the like.

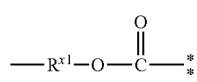
(X-1)

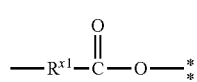
(X-2)

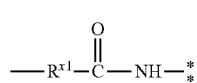
(X-3)

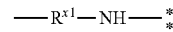
(X-4)

(X-5)

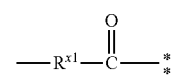
(X-6)

wherein $R^{x1}$ is a divalent chain hydrocarbon group having 1 to 30 carbon atoms, a divalent alicyclic hydrocarbon group having 3 to 30 carbon atoms, or a divalent aromatic hydrocarbon group having 6 to 30 carbon atoms, and * is a bonding site bonded to the carbon atom of the carbonyl group in the formula (5-2).

Examples of the structural unit (V) include structural units respectively represented by the following formulas (5-1a), (5-1b), and (5-2a) to (5-2e), and the like.

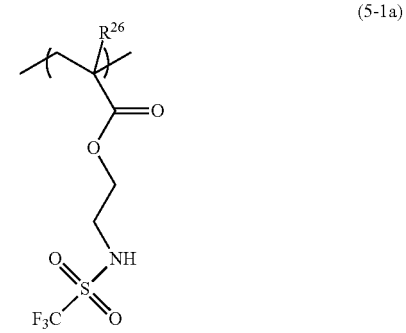
(5-1a)

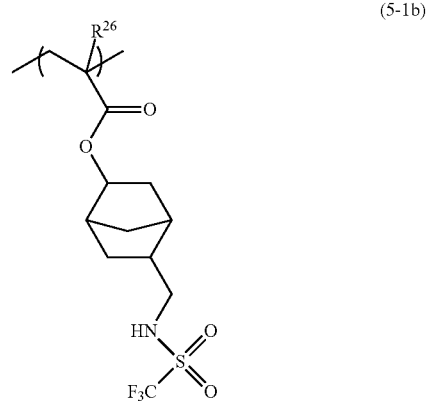
(5-1b)

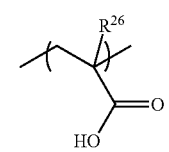
(5-2a)

(5-2b)

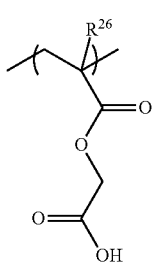

(5-2c)

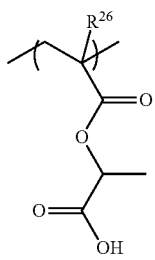

(5-2d)

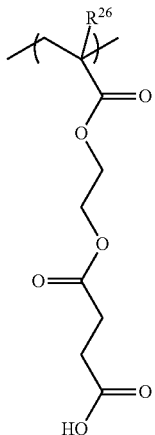

(5-2e)

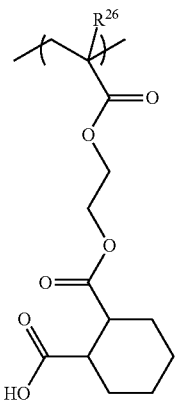

wherein $R^{26}$ is a hydrogen atom, a methyl group, or a trifluoromethyl group.

The content of the structural unit (V) in the polymer [A] (when the polymer [A] is used as the base polymer or the water-repellent additive) is normally 50 mol % or less, preferably 0 to 30 mol %, and more preferably 0 to 20 mol %, based on the total structural units included in the polymer [A]. When the content of the structural unit (V) is within the above range, water repellency during liquid immersion lithography and affinity for a developer during development can be achieved in a well-balanced manner.

Structural Unit (VI)

The polymer [A] may include the structural unit (VI) that includes a lactone structure. When the polymer [A] includes the structural unit (VI), the resulting resist film exhibits improved affinity for an alkaline developer. Moreover, the resist film exhibits improved adhesion to the substrate.

Examples of the structural unit (VI) include a structural unit represented by the following formula (6), and the like.

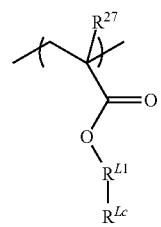

(6)

wherein $R^{27}$ is a hydrogen atom, a fluorine atom, a methyl group, or a trifluoromethyl group, $R^{L1}$ is a single bond or a divalent linking group, and $R^{Lc}$ is a monovalent organic group having a lactone structure.

Examples of the divalent linking group represented by $R^{L1}$ include the groups mentioned above in connection with the divalent linking group represented by $R^{25}$ (structural unit (V)), and the like.

Examples of the monovalent organic group having a lactone structure represented by $R^{Lc}$ include groups respectively represented by the following formulas (Lc-1) to (Lc-6), and the like.

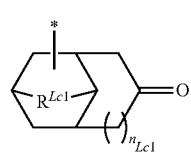

(Lc-1)

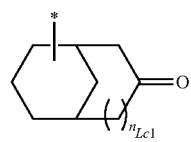

(Lc-2)

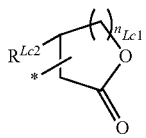

(Lc-3)

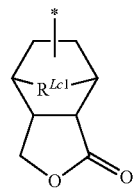

(Lc-4)

(Lc-5)

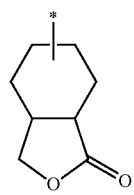

(Lc-6)

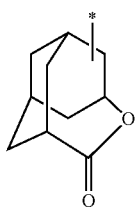

wherein $R^{Lc1}$ is an oxygen atom or a methylene group, $R^{Lc2}$ is a hydrogen atom or an alkyl group having 1 to 4 carbon atoms, $n_{Lc1}$ is 0 or 1, $n_{Lc2}$ is an integer from 0 to 3, and * is a bonding site bonded to $R^{L1}$ in the formula (7). Note that the groups respectively represented by the formulas (Lc-1) to (Lc-6) may be substituted with a substituent.

Examples of a substituent that may substitute the groups respectively represented by the formulas (Lc-1) to (Lc-6) include the substituents mentioned above in connection with $R^C$ included in the structural unit (I), and the like.

Examples of the structural unit (VI) include the structural units disclosed in paragraphs [0054] to [0057] of Japanese Patent Application Publication (KOKAI) No. 2007-304537, the structural units disclosed in paragraphs [0086] to [0088] of Japanese Patent Application Publication (KOKAI) No. 2008-088343, structural units respectively represented by the following formulas (6-1) to (6-14), and the like.

(6-1)

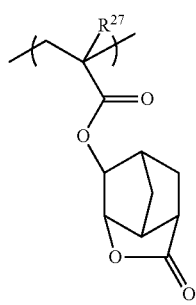

(6-2)

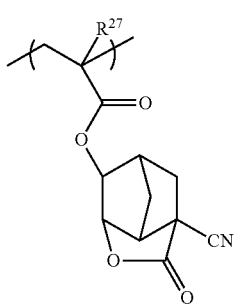

(6-3)

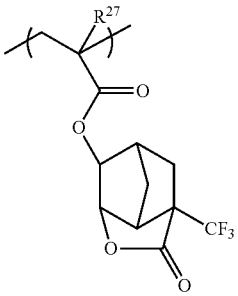

(6-4)

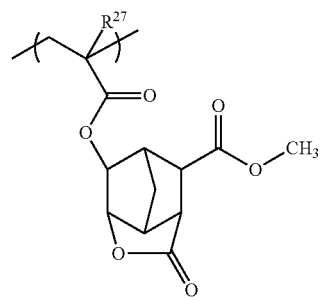

(6-5)

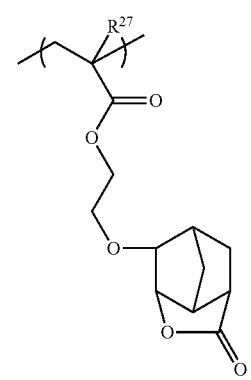

(6-6)

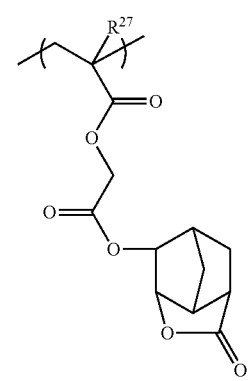

(6-7) 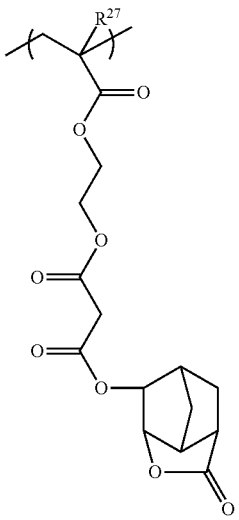

(6-8) 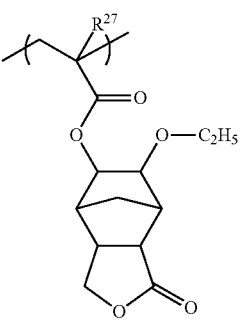

(6-9) 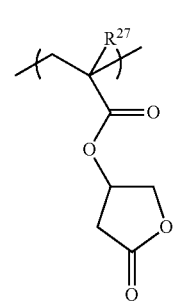

(6-10) 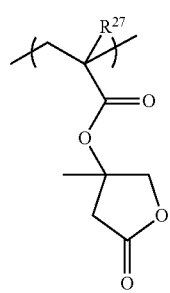

(6-11) 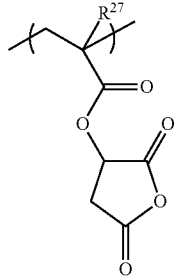

(6-12) 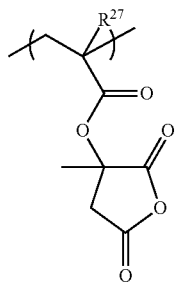

(6-13) 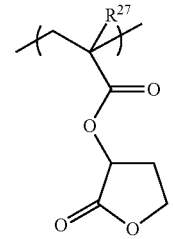

(6-14) 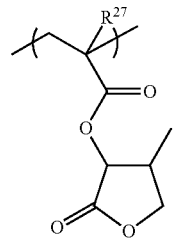

wherein $R^{27}$ is the same as defined for the formula (6).

Among these, the structural unit represented by the formula (6-1) is preferable since the resulting resist film exhibits improved affinity for an alkaline developer, and improved adhesion to the substrate.

The polymer [A] may include only one type of the structural unit (VI), or may include two or more types of the structural unit (VI). Examples of a preferable monomer that produces the structural unit (VI) include the monomers disclosed in paragraph [0043] of WO2007/116664.

When the polymer [A] is used as the base polymer, the content of the structural unit (VI) in the polymer [A] is preferably 5 to 75 mol %, more preferably 15 to 65 mol %, and particularly more preferably 25 to 55 mol %, based on the total structural units included in the polymer [A]. If the content of the structural unit (VI) is less than 5 mol %, the resulting resist film may be removed from the substrate due to insufficient adhesion to the substrate. If the content of the structural unit (VI) exceeds 75 mol %, the pattern shape may deteriorate due to a decrease in contrast after dissolution.

When the polymer [A] is used as the water-repellent additive, the content of the structural unit (VI) in the polymer [A] is normally 50 mol % or less, preferably 5 to 40 mol %, and more preferably 5 to 20 mol %, based on the total structural units included in the polymer [A]. When the content of the structural unit (VI) is within the above range, the surface of the resulting resist film exhibits improved affinity for an alkaline developer.

Structural Unit (VII)

The polymer [A] may include the structural unit (VII) that includes a cyclic carbonate structure. When the polymer [A] includes the structural unit (VII), the resulting resist film exhibits improved affinity for an alkaline developer. Moreover, the resist film exhibits improved adhesion to the substrate. Examples of the structural unit (VII) include a structural unit represented by the following formula (7), and the like.

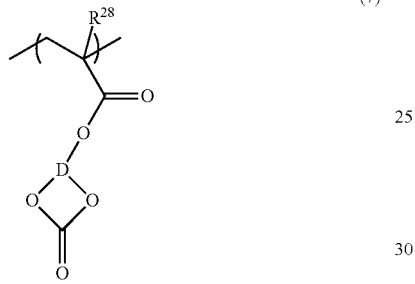

(7)

wherein $R^{28}$ is a hydrogen atom, a fluorine atom, a methyl group, or a trifluoromethyl group, and D is a trivalent chain hydrocarbon group having 1 or 30 carbon atoms, a trivalent alicyclic hydrocarbon group having 3 or 30 carbon atoms, or a trivalent aromatic hydrocarbon group having 6 or 30 carbon atoms, provided that D may include an oxygen atom, a carbonyl group, or —NH— in the skeleton, and may be substituted with a substituent.

Examples of a substituent that may substitute D include the substituent $R^S$ and the like.

A monomer that produces the structural unit represented by the formula (7) may be synthesized using a known method such as the method described in Tetrahedron Letters, Vol. 27, No. 32, p. 3741 (1986), Organic Letters, Vol. 4, No. 15, p. 2561 (2002), or the like.

Structural units respectively represented by the following formulas (7-1) to (7-22) are preferable as the structural unit (VII).

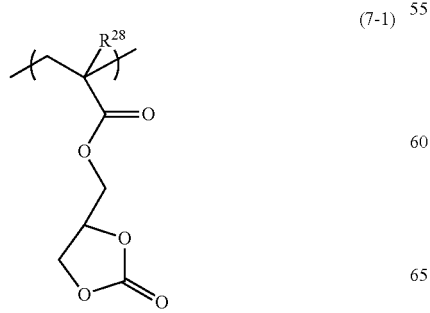

(7-1)

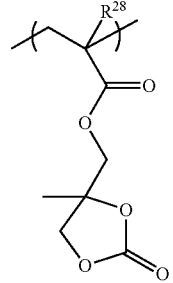

(7-2)

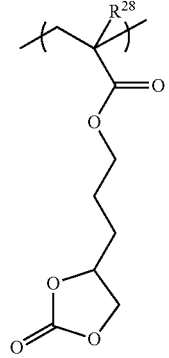

(7-3)

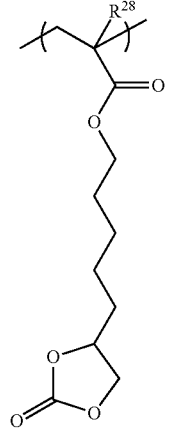

(7-4)

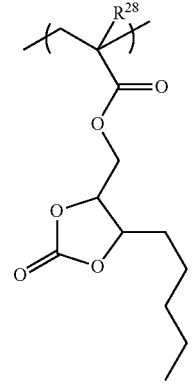

(7-5)

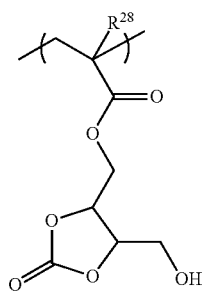
(7-6)
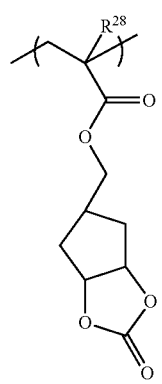
(7-7)
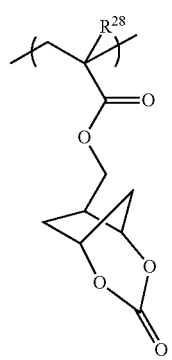
(7-8)
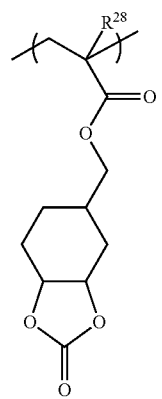
(7-9)
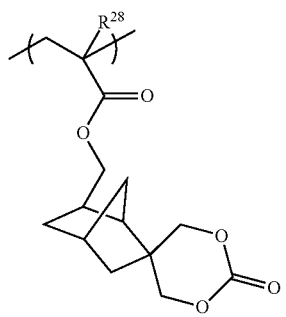
(7-10)
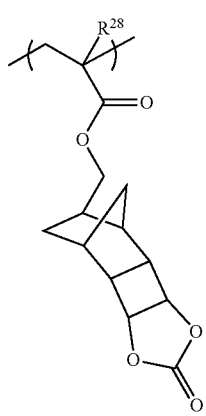
(7-11)
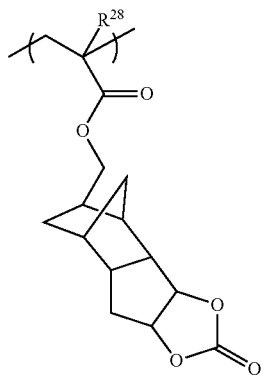
(7-12)
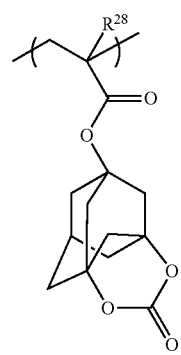
(7-13)

(7-14)
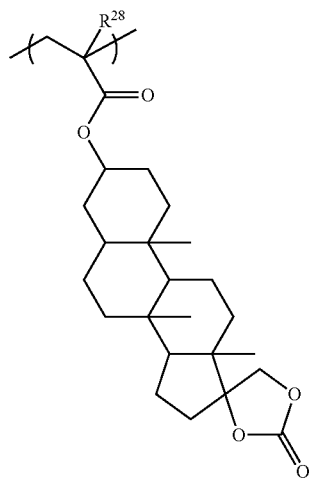
(7-15)
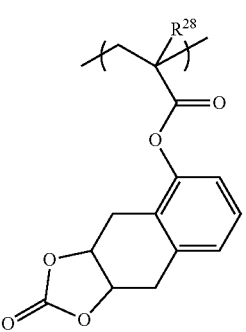
(7-16)
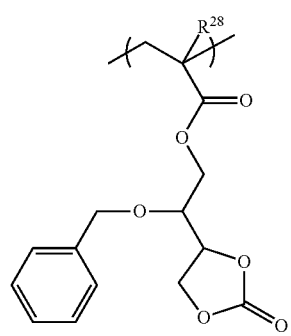
(7-17)
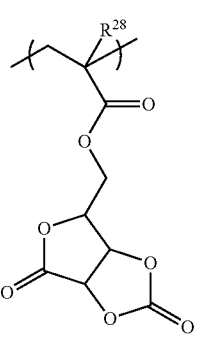
(7-18)
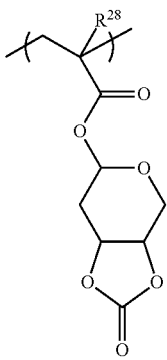
(7-19)
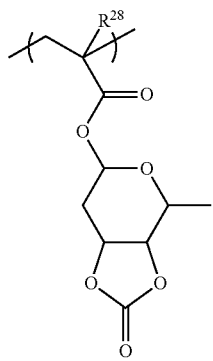
(7-20)
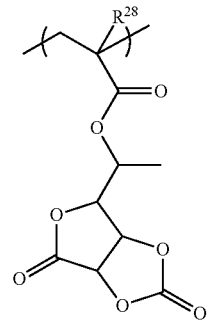
(7-21)
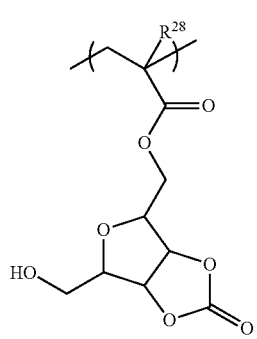

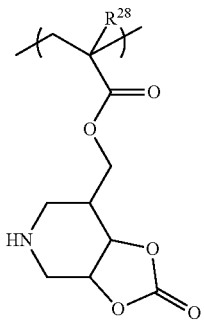

(7-22)

wherein $R^{28}$ is the same as defined for the formula (7).

When the polymer [A] is used as the base polymer, the content of the structural unit (VII) in the polymer [A] is preferably 5 to 75 mol %, more preferably 15 to 65 mol %, and particularly more preferably 25 to 55 mol %, based on the total structural units included in the polymer [A]. If the content of the structural unit (VII) is less than 5 mol %, the resulting resist film may be removed from the substrate due to insufficient adhesion to the substrate. If the content of the structural unit (VII) exceeds 75 mol %, the pattern shape may deteriorate due to a decrease in contrast after dissolution.

When the polymer [A] is used as the water-repellent additive, the content of the structural unit (VII) in the polymer [A] is normally 50 mol % or less, preferably 5 to 40 mol %, and more preferably 5 to 20 mol %, based on the total structural units included in the polymer [A]. When the content of the structural unit (VII) is within the above range, the surface of the resulting resist film exhibits improved affinity for an alkaline developer.

Additional Structural Unit

The polymer [A] may include an additional structural unit other than the above structural units. Examples of a polymerizable unsaturated monomer that produces the additional structural unit include the monomers disclosed in paragraphs [0065] to [0085] of WO2007/116664, and the like.

The additional structural unit is preferably a structural unit derived from 3-hydroxyadamantan-1-yl(meth)acrylate, 3,5-dihydroxyadamantan-1-yl(meth)acrylate, 2-hydroxyethyl(meth)acrylate, 2-hydroxypropyl(meth)acrylate, or 3-hydroxypropyl(meth)acrylate.

The content of the additional structural unit in the polymer [A] (when the polymer [A] is used as the base polymer or the water-repellent additive) is normally 50 mol % or less, preferably 5 to 40 mol %, and more preferably 5 to 20 mol %, based on the total structural units included in the polymer [A]. When the content of the additional structural unit is within the above range, the surface of the resulting resist film exhibits improved affinity for an alkaline developer.

Preferable Examples of Polymer [A]

The polymer [A] may be a polymer that includes the structural unit (I), and at least one structural unit selected from the group consisting of the structural unit (VI) that includes a lactone structure and the structural unit (VII) that includes a cyclic carbonate structure (hereinafter referred to as "polymer [A1]").

Polymer [A1]

The polymer [A1] exhibits the above characteristics due to the structural unit (I), and ensures that the resulting resist film exhibits improved affinity for an alkaline developer due to the structural unit (VI) that includes a lactone structure and/or the structural unit (VII) that includes a cyclic carbonate structure. This makes it possible to suppress a situation in which the resin remains undissolved in the exposed area, suppress occurrence of scum and bridge defects, and further improve the resist pattern-forming capability and the LWR performance. The polymer [A1] having such characteristics may suitably be used as the base polymer.

The polymer [A] may be at least one polymer selected from the group consisting of a polymer that includes the structural unit (I) and a structural unit (F) that includes a fluorine atom, and a polymer that includes a structural unit (I) that includes a fluorine atom (hereinafter referred to as "polymer [A2]").

Polymer [A2]

The polymer [A2] that includes the structural unit (F) that includes a fluorine atom and/or the structural unit (I) that includes a fluorine atom exhibits high hydrophobicity, and functions as the water-repellent additive. When the polymer [A2] includes the structural unit (I), it is possible to obtain a resist pattern having an excellent pattern shape and excellent LWR performance even when the PEB temperature is reduced. Moreover, since it is possible to suppress a situation in which the water-repellent additive that is unevenly distributed in the surface area of the resist remains undissolved in an alkaline developer, occurrence of scum and bridge defects can be significantly suppressed.

Examples of the structural unit (F) that includes a fluorine atom include the structural unit (II), the structural unit (III), and the structural units (V) to (VII) wherein $R^{26}$, $R^{27}$, and $R^{28}$ are a fluorine atom or a trifluoromethyl group, or a substituent that includes a fluorine atom is provided.

Examples of the structural unit (I) that includes a fluorine atom include the structural unit represented by the formula (1) wherein a substituent that substitutes $R^C$ includes a fluorine atom, the structural unit represented by the formula (1) wherein $R^1$ is a fluorine atom or a trifluoromethyl group, and the like.

It is preferable that the polymer [A2] have a fluorine atom content higher than that of a polymer used as the base polymer in order to ensure that the polymer [A2] advantageously functions as the water-repellent additive. When the polymer [A2] has a fluorine atom content higher than that of a polymer used as the base polymer, the polymer [A2] tends to be unevenly distributed in the surface area of the resulting resist film. Therefore, the surface of the resist film more effectively exhibits excellent characteristics (e.g., high draining capability) due to the hydrophobicity of the polymer [A2]. The fluorine atom content in the additional polymer [E] (described later) is preferably 5 mass % or more, more preferably 7 mass % or more, and still more preferably 10 mass % or more. The fluorine atom content in the polymer [A1] is preferably less than 5 mass %, more preferably 3 mass % or less, and still more preferably 1 mass % or less. The fluorine atom content may be calculated from the $^{13}$C-NMR analysis results for the structure of the polymer.

It is particularly preferable that the radiation-sensitive resin composition include both the polymer [A1] and the polymer [A2] as the polymer [A]. When the radiation-sensitive resin composition includes both the polymer [A1] and the polymer [A2], the polymer [A1] functions as the base polymer, and the polymer [A2] functions as the water-repellent additive. Since the polymer [A1] and the polymer [A2] are designed so that the acid-labile group sufficiently dissociates even if the PEB temperature is reduced, a situation in which the resulting resist film remains undissolved in an alkaline developer is further suppressed, for example. This makes it possible to further improve the pattern-forming capability and the LWR performance of the resulting resist pattern while further suppressing occurrence of scum and bridge defects.

Method for Synthesizing Polymer [A]

The polymer [A] may be synthesized using a normal method such as radical polymerization. The polymer [A] may be synthesized by adding a solution including a monomer and a radical initiator dropwise to a reaction solvent or a solution including a monomer to effect polymerization, adding a solution including a monomer and a solution including a radical initiator dropwise to a reaction solvent or a solution including a monomer to effect polymerization, or adding a plurality of solutions respectively including a monomer and a solution including a radical initiator dropwise to a reaction solvent or a solution including a monomer to effect polymerization, for example.

The reaction (polymerization) temperature is appropriately determined depending on the type of radical initiator, but is normally 30 to 180° C., preferably 40 to 160° C., and more preferably 50 to 140° C. The dropwise addition time is determined depending on the reaction temperature, the type of radical initiator, the type of monomer, and the like, but is normally 30 minutes to 8 hours, preferably 45 minutes to 6 hours, and more preferably 1 to 5 hours. The total reaction time including the dropwise addition time is normally 30 minutes to 8 hours, preferably 45 minutes to 7 hours, and more preferably 1 to 6 hours.

Examples of the radical initiator include 2,2'-azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2-azobisisobutyrate, and the like. These radical initiators may be used in combination.

The solvent used for polymerization is not particularly limited as long as the solvent does not hinder polymerization of each monomer, and can dissolve each monomer. Examples of the solvent include alcohol-based solvents, ketone-based solvents, amide-based solvents, ester-based solvents, lactone-based solvents, nitrile-based solvents, and the like. These solvents may be used in combination.

The polymer obtained by polymerization may be collected by re-precipitation. An alcohol-based solvent or the like may be used as a re-precipitation solvent.

A molecular weight modifier may be used during polymerization for synthesizing the polymer [A] in order to adjust the molecular weight of the polymer [A]. Examples of the molecular weight modifier include halogenated hydrocarbons such as chloroform and carbon tetrabromide; mercaptans such as n-hexylmercaptan, n-octylmercaptan, n-dodecylmercaptan, t-dodecylmercaptan, and thioglycolic acid; xanthogens such as dimethyl xanthogen sulfide and diisopropyl xanthogen disulfide; terpinolene; an α-methylstyrene dimer; and the like.

The polystyrene-reduced weight average molecular weight (Mw) of the polymer [A] determined by gel permeation chromatography (GPC) is preferably 1000 to 20,000, and more preferably 2000 to 10,000. When the Mw of the polymer [A] is within the above range, the radiation-sensitive resin composition exhibits improved lithographic performance (e.g., sensitivity and LWR performance).

The content of low-molecular-weight components in the polymer [A] is preferably 0.2 mass % or less, more preferably 0.1 mass % or less, and particularly preferably 0.06 mass % or less. When the content of low-molecular-weight components is within the above range, the development contrast can be further improved. Note that the low-molecular-weight components refer to components having a molecular weight of less than 1000.

The ratio (Mw/Mn) (dispersity) of the Mw to the polystyrene-reduced number average molecular weight (Mn) of the polymer [A] determined by GPC is normally 1 to 5, preferably 1 to 3, and more preferably 1 to 2. When the dispersity (Mw/Mn) of the polymer [A] is within the above range, the radiation-sensitive resin composition exhibits improved lithographic performance (e.g., sensitivity and LWR performance) and etching resistance. Note that the terms "Mw" and "Mn" used herein refer to values determined by GPC under the following conditions.

Column: G2000HXL×2, G3000HXL×1, G4000HXL×1 (manufactured by Tosoh Corporation)
Eluant: tetrahydrofuran
Column temperature: 40° C.
Flow rate: 1.0 ml/min
Detector: differential refractometer
Standard: monodisperse polystyrene Acid Generator [B]

The radiation-sensitive resin composition includes the acid generator [B]. The acid generator [B] generates an acid upon exposure, and the acid-labile group included in the structural unit (I) included in the polymer [A] dissociates due to the acid generated by the acid generator [B] to produce a carboxyl group, for example. As a result, the polymer [A] exhibits increased polarity, and becomes soluble in a developer in an exposed area. The acid generator [B] may be included in the radiation-sensitive resin composition as a compound (described below) and/or may be included in the polymer.

Examples of the acid generator [B] include onium salt compounds, N-sulfonyloxyimide compounds, halogen-containing compounds, diazoketone compounds, and the like.

Examples of the onium salt compounds include sulfonium salts, tetrahydrothiophenium salts, iodonium salts, phosphonium salts, diazonium salts, pyridinium salts, and the like. Among these, sulfonium salts and iodonium salts are preferable.

Examples of the sulfonium salts include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-(1-adamantyl)-1,1-difluoroethanesulfonate, triphenylsulfonium 2-(adamantylcarbonyloxy)-1,1,3,3,3-pentafluoropropanesulfonate, triphenylsulfonium norbornanesultonyloxycarbonyldifluoromethanesulfonate, triphenylsulfonium 3-piperidylsulfonyl-1,1,2,2,3,3-hexafluoropropane-1-sulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)hexane-1-sulfonate, and the like.

Examples of the tetrahydrothiophenium salts include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesufonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Examples of the iodonium salts include diphenyliodonium trifluoromethanesulfonate, diphenyliodonium nonafluoro-n-butanesufonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesufonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the N-sulfonyloxyimide compounds include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Among these, sulfonium salts are preferable, and triphenylsulfonium 2-(1-adamantyl)-1,1-difluoroethanesulfonate, triphenylsulfonium 2-(adamantylcarbonyloxy)-1,1,3,3,3-pentafluoropropanesulfonate, triphenylsulfonium norbomanesultonyloxycarbonyldifluoromethanesulfonate, and triphenylsulfonium 3-piperidylsulfonyl-1,1,2,2,3,3-hexafluoropropane-1-sulfonate are more preferable.

These acid generators [B] may be used in combination. The acid generator [B] is normally used in an amount of 0.1 to 30 parts by mass, and preferably 1 to 25 parts by mass, based on 100 parts by mass of the polymer [A], from the viewpoint of ensuring that the resulting resist exhibits sufficient sensitivity and developability. If the amount of the acid generator [B] is less than 0.1 parts by mass, the sensitivity and the developability of the radiation-sensitive resin composition may deteriorate. If the amount of the acid generator [B] exceeds 30 parts by mass, the desired resist pattern may not be obtained due to a decrease in transparency to exposure light.

Solvent [C]

The radiation-sensitive resin composition normally includes the solvent [C]. A compound that homogenously dissolves or disperses each component, and does not react with each component is used as the solvent [C]. Examples of the solvent [C] include alcohols, ethers, ketones, amides, esters, and the like. These solvents may be used in combination.

Examples of the alcohols include monohydric alcohols such as methanol, ethanol, n-propanol, isopropanol, n-butanol, isobutanol, sec-butanol, tert-butanol, n-pentanol, iso-pentanol, 2-methylbutanol, sec-pentanol, t-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, and diacetone alcohol; polyhydric alcohols such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, and tripropylene glycol; polyhydric alcohol partial ethers such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethyl butyl ether, diethylene glycol monomethyl ether, diethylene glycol monoethyl ether, diethylene glycol monopropyl ether, diethylene glycol monobutyl ether, diethylene glycol monohexyl ether, propylene glycol methyl ether, propylene glycol monoethyl ether, propylene glycol monopropyl ether, propylene glycol monobutyl ether, dipropyleneglycol monomethylether, dipropylene glycol monoethyl ether, and dipropylene glycol monopropyl ether; and the like.

Examples of the ethers include diethyl ether, dipropyl ether, dibutyl ether, diphenyl ether, methoxybenzene, and the like.

Examples of the ketones include acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, diisobutyl ketone, trimethylenonane, cyclopentanone, cyclohexanone, cycloheptanone, cyclooctanone, methylcyclohexanone, 2,4-pentanedione, acetonylacetone, acetophenone, and the like.

Examples of the amides include N,N'-dimethylimidazolidinone, N-methylformamide, N,N-dimethylformamide, N,N-diethylformamide, acetamide, N-methylacetamide, N,N-dimethylacetamide, N-methylpropioneamide, N-methylpyrrolidone, and the like.

Examples of the esters include methyl acetate, ethyl acetate, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the hydrocarbons include aliphatic hydrocarbons such as n-pentane, isopentane, n-hexane, isohexane, n-heptane, isoheptane, 2,2,4-trimethylpentane, n-octane, isooctane, cyclohexane, and methylcyclohexane; aromatic hydrocarbons such as benzene, toluene, xylene, mesitylene, ethylbenzene, trimethylbenzene, methylethylbenzene, n-propylbenzene, isopropylbenzene, diethylbenzene, isobutylbenzene, triethylbenzene, diisopropylbenzene, and n-amylnaphthalene; and the like.

Among these, esters and ketones are preferable, and propylene glycol monomethyl ether acetate and cyclohexanone are more preferable.

Acid Diffusion Controller [D]

It is preferable that the radiation-sensitive resin composition include the acid diffusion controller [D]. The acid diffusion controller [D] controls a phenomenon in which the acid generated by the acid generator [B] upon exposure is diffused in the resist film, and suppresses undesired chemical reactions in the unexposed area. When the radiation-sensitive resin composition further includes the acid diffusion controller [D], it is possible to form a resist pattern with excellent developability and reduced LWR. The acid diffusion controller [D] may be included in the radiation-sensitive resin composition as a compound (described below) and/or may be included in the polymer.

Examples of the acid diffusion controller [D] include N-t-alkoxycarbonyl group-containing amino compounds, tertiary amine compounds, quaternary ammonium hydroxide compounds, cyclic amines, and the like.

Examples of the N-t-alkoxycarbonyl group-containing amino compounds include N-t-butoxycarbonyldi-N-octylamine, N-t-amyloxycarbonyldi-N-octylamine, N-t-butoxycarbonyldi-N-nonylamine, N-t-amyloxycarbonyldi-N-nonylamine, N-t-butoxycarbonyldi-N-decylamine, N-t-amyloxycarbonyldi-N-decylamine, N-t-butoxycarbonyldicyclohexylamine, N-t-amyloxycarbonyldicyclohexylamine, N-t-butoxycarbonyl-1-adamantylamine, N-t-amyloxycarbonyl-1-adamantylamine, N-t-butoxycarbonyl-2-adamantylamine, N-t-amyloxycarbonyl-2-adamantylamine, N-t-butoxycarbonyl-N-methyl-1-adamantylamine, N-t-amyloxycarbonyl-N-methyl-1-adamantylamine, N-t-butoxycarbonylbenzimidazole, N-t-amyloxycarbonyl-2-methylbenzimidazole, N-t-butoxycarbonyl-2-phenylbenzimidazole, N-t-amyloxycarbonyl-2-phenylbenzimidazole, N-t-butoxycarbonyl-4-hydroxypiperidine, N-t-amyloxycarbonyl-4-hydroxypiperidine, and the like.

Examples of the tertiary amine compounds include tri(cyclo)alkylamines such as triethylamine, tri-n-propylamine, tri-n-butylamine, tri-n-pentylamine, tri-n-hexylamine, tri-n-heptylamine, tri-n-octylamine, cyclohexyldimethylamine, dicyclohexylmethylamine, and tricyclohexylamine, aromatic amines such as aniline, N-methylaniline, N,N-dimethylaniline, 2-methylaniline, 3-methylaniline, 4-methylaniline, 4-nitroaniline, 2,6-dimethylaniline, and 2,6-diisopropylaniline, alkanolamines such as triethanolamine and N,N-di(hydroxyethyl)aniline, N,N,N',N'-tetramethylethylenediamine, N,N,N',N'-tetrakis(2-hydroxypropyl)ethylenediamine, 1,3-bis[1-(4-aminophenyl)-1-methylethyl]benzenetetramethylenediamine, bis(2-dimethylaminoethyl) ether, bis(2-diethylaminoethyl) ether, and the like.

Examples of the quaternary ammonium hydroxide compounds include tetra-n-propylammonium hydroxide, tetra-n-butylammonium hydroxide, and the like.

Examples of the cyclic amines include pyridines such as pyridine and 2-methylpyridine, morpholines such as N-propylmorpholine and N-(undecylcarbonyloxyethyl)morpholine, pyrazine, pyrazole, and the like.

An onium salt compound that decomposes upon exposure, and loses basicity (i.e., acid diffusion controllability) may also be used as the acid diffusion controller [D].

Examples of the onium salt compound include a sulfonium salt compound represented by the following formula (8-1), an iodonium salt compound represented by the following formula (8-2), and the like.

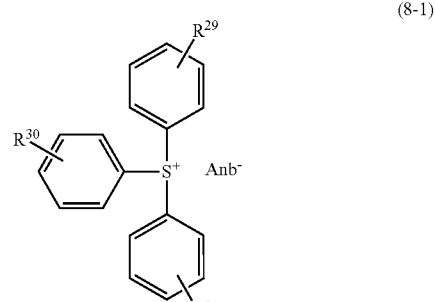

(8-1)

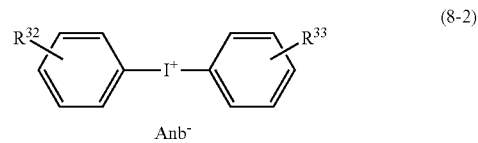

(8-2)

wherein $R^{29}$ to $R^{33}$ are independently a hydrogen atom, an alkyl group, an alkoxy group, a hydroxyl group, or a halogen atom, Anb$^-$ is OH$^-$, $R^{34}$—COO$^-$, $R^{34}$—SO$_3^-$, or the anion represented by the following formula (9), and $R^{34}$ is an alkyl group, an aryl group, or an aralkyl group.

(9)

Examples of the sulfonium salt compound and the iodonium salt compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate, bis(4-t-butylphenyl)iodonium 10-camphorsulfonate, diphenyliodonium 10-camphorsulfonate, triphenylsulfonium 10-camphorsulfonate, 4-t-butoxyphenyldiphenylsulfonium 10-camphorsulfonate, and the like. Among these, triphenylsulfonium 10-camphorsulfonate is preferable.

These acid diffusion controllers [D] may be used in combination. The acid diffusion controller [D] is preferably used in an amount of 0.1 to 20 parts by mass, and more preferably 0.5 to 15 parts by mass, based on 100 parts by mass of the polymer [A]. When the amount of the acid diffusion controller [D] is within the above range, the pattern developability and the LWR performance of the resulting radiation-sensitive resin composition are further improved.

Additional Polymer [E]

The radiation-sensitive resin composition may include the additional polymer [E] as the polymer component in addition to the polymer [A]. Examples of the additional polymer [E] include a polymer that includes at least one structural unit selected from the group consisting of the structural unit (II) to (VII) and the additional structural unit, and the like.

The Mw of the additional polymer [E] is preferably 1500 to 20,000, and more preferably 2000 to 15,000. When the Mw of the additional polymer [E] is within the above range, the radiation-sensitive resin composition exhibits improved lithographic performance (e.g., sensitivity and LWR performance). The ratio (Mw/Mn) of the Mw to the Mn of the additional polymer [E] is normally 1 to 3, and preferably 1 to 2.

The additional polymer [E] is preferably used in an amount of 0 to 20 parts by mass, and more preferably 0.1 to 10 parts by mass, based on 100 parts by mass of the polymer [A]. When the amount of the additional polymer [E] is within the above range, the water repellency and the elution resistance of the surface of the resulting resist film can be further improved.

Method for Synthesizing Additional Polymer [E]

The additional polymer [E] may be synthesized in the same manner as the polymer [A] by polymerizing a monomer that produces each structural unit in an appropriate solvent in the presence of a radical initiator, for example. The reaction (polymerization) temperature is normally 40 to 150° C., and preferably 50 to 120° C. The reaction (polymerization) time is normally 1 to 48 hours, and preferably 1 to 24 hours.

Additional Optional Component

The radiation-sensitive resin composition may include an uneven distribution promoter, a surfactant, a sensitizer, or the like as an additional optional component. Note that the radiation-sensitive resin composition may include only one type of each additional optional component, or may include two or more types of each additional optional component.

Uneven Distribution Promoter

The uneven distribution promoter causes the water-repellent additive included in the radiation-sensitive resin composition to be more efficiently unevenly distributed in the surface area of the resist film. The amount of the water-repellent additive used to produce the radiation-sensitive resin composition can be reduced by adding the uneven distribution promoter to the radiation-sensitive resin composition. This makes it possible to further suppress elution of components from the resist film into an immersion liquid, or implement high-speed liquid immersion lithography via a high-speed scan without impairing the basic resist performance (e.g., LWR, development defect resistance, and pattern collapse resistance), so that the hydrophobicity of the surface of the resist film that suppresses defects (e.g., watermark defects) that may occur due to liquid immersion lithography can be improved. Examples of the uneven distribution promoter include a low-molecular-weight compound having a relative dielectric constant of 30 to 200 and a boiling point at 1 atmosphere of 100° C. or more. Examples of such a compound include lactone compounds, carbonate compounds, nitrile compounds, polyhydric alcohols, and the like.

Examples of the lactone compounds include γ-butyrolactone, valerolactone, mevalonic lactone, norbornanelactone, and the like.

Examples of the carbonate compounds include propylene carbonate, ethylene carbonate, butylene carbonate, vinylene carbonate, and the like.

Examples of the nitrile compounds include succinonitrile and the like. Examples of the polyhydric alcohols include glycerol and the like.

Among these, the lactone compounds and the carbonate compounds are preferable, γ-butyrolactone and propylene carbonate are more preferable, and γ-butyrolactone is particularly preferable.

Surfactant

The surfactant improves applicability, striation, developability, and the like. Examples of the surfactant include nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate. Examples of a commercially available surfactant include KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like.

Sensitizer

The sensitizer increases the amount of acid generated by the acid generator [B], and improves the apparent sensitivity of the radiation-sensitive resin composition. Examples of the sensitizer include carbazoles, acetophenones, benzophenones, naphthalenes, phenols, biacetyl, eosine, rose bengal, pyrenes, anthracenes, phenothiazines, and the like.

Preparation of Radiation-Sensitive Resin Composition

The radiation-sensitive resin composition may be prepared by mixing the polymer [A], the acid generator [B], the acid diffusion controller [D], the additional polymer [E], and the additive [G] in the solvent [C] in a given ratio, for example. The radiation-sensitive resin composition is normally prepared by dissolving the components in the solvent so that the total solid content is 1 to 30 mass %, and preferably 1.5 to 25 mass %, and filtering the solution through a filter having a pore size of about 200 nm, for example.

Resist Pattern-Forming Method

A resist pattern-forming method according to one embodiment of the invention includes forming a resist film on a substrate using the radiation-sensitive resin composition (hereinafter may be referred to as "resist film-forming step"), exposing the resist film (hereinafter may be referred to as "exposure step"), heating the exposed resist film (hereinafter may be referred to as "heating step"), and developing the heated resist film (hereinafter may be referred to as "development step"). Each step is described in detail below.

Resist Film-Forming Step

In the resist film-forming step, the resist film is formed on the substrate using the radiation-sensitive resin composition. A silicon wafer, an aluminum-coated wafer, or the like may be used as the substrate. An organic or inorganic antireflective film as disclosed in Japanese Patent Publication (KOKOKU) No. 6-12452, Japanese Patent Application Publication (KOKAI) No. 59-93448, or the like may be formed on the substrate.

The radiation-sensitive resin composition may be applied by spin coating, cast coating, roll coating, or the like. The thickness of the resist film is normally 10 to 1000 nm, and preferably 10 to 500 nm.

The resist film formed by applying the radiation-sensitive resin composition may optionally be prebaked (PB) to vaporize the solvent from the film. The PB temperature is appropriately selected depending on the composition of the radiation-sensitive resin composition, but is normally about 30 to about 200° C., and preferably 50 to 150° C.

Exposure Step

In the exposure step, the desired area of the resist film formed by the resist film-forming step is subjected to reduced projection exposure via a mask having a specific pattern and an optional immersion liquid. For example, the desired area of the resist film may be subjected to reduced projection exposure via an isolated line pattern mask to form an isolated trench pattern. The resist film may be exposed two or more times. Examples of the immersion liquid used for exposure include water, a fluorine-containing inert liquid, and the like. It is preferable that the immersion liquid be a liquid that is transparent to the exposure wavelength and has a temperature coefficient of refractive index as small as possible so that distortion of an optical image projected onto the film is minimized. When using ArF excimer laser light (wavelength: 193 nm) as the exposure light, it is preferable to use water as the immersion liquid from the viewpoint of availability and ease of handling in addition to the above properties. When using water as the immersion liquid, a small amount of an additive that decreases the surface tension of water and increases the surface activity of water may be added to water. It is preferable that the additive does not dissolve the resist layer formed on the wafer, and does not affect the optical coating formed on the bottom surface of the lens. Distilled water is preferably used as the water.

The light used for exposure is appropriately selected from ultraviolet rays, deep ultraviolet rays, extreme ultraviolet (EUV) light, X-rays, charged particle rays, and the like depending on the type of the acid generator [B]. It is preferable to use deep ultraviolet rays such as ArF excimer laser light or KrF excimer laser light (wavelength: 248 nm), or EUV light. The exposure conditions (e.g., dose) are appropriately selected depending on the composition of the radiation-sensitive resin composition, the type of additive, and the like.

Heating Step

In the heating step, the exposed resist film is subjected to PEB. The acid-labile group included in the radiation-sensitive resin composition dissociates smoothly due to PEB. The PEB temperature has been selected within the range from 90 to 180° C. However, the PEB temperature can be reduced to 90° C. or less by utilizing the radiation-sensitive resin composition according to one embodiment of the invention.

Development Step

In the development step, the resist film that has been exposed and heated is developed using a developer. After development, the resist film is normally rinsed with water, and dried. When performing alkali development, the developer is preferably an alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water, for example.

When performing organic solvent development, the developer may be at least one organic solvent selected from the group consisting of alkyl carboxylates having 3 to 7 carbon atoms and dialkyl ketones having 3 to 10 carbon atoms. When the above organic solvent is used as the developer, the unexposed area is developed to obtain a pattern that is reversed as compared with that obtained using an alkaline aqueous solution.

Examples of the alkyl carboxylates having 3 to 7 carbon atoms include diethyl carbonate, propylene carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, and the like.

Examples of the dialkyl ketones having 3 to 10 carbon atoms include acetone, 2-butanone, methyl isoamyl ketone, methyl n-propyl ketone, methyl n-butyl ketone, diethyl ketone, methyl isobutyl ketone, methyl n-pentyl ketone, ethyl n-butyl ketone, and the like.

Among these, n-butyl acetate and methyl isoamyl ketone are preferable. These organic solvents may be used either alone or in combination.

Examples of the development method include a dipping method that immerses the substrate in a bath filled with the developer for a given time, a puddle method that allows the developer to be present on the surface of the substrate for a given time due to surface tension, a spray method that sprays the developer onto the surface of the substrate, a dynamic dispensing method that applies the developer to the substrate that is rotated at a constant speed while scanning with a developer application nozzle at a constant speed, and the like.

Polymer

A polymer according to one embodiment of the invention includes the structural unit (I) represented by the formula (1). Since the polymer includes the structural unit (I) that includes an acid-labile group that has a very high dissociation capability, the polymer may suitably be used as a component of the radiation-sensitive resin composition. The radiation-sensitive resin composition that includes the polymer makes it possible to reduce the PEB temperature, and can form a resist pattern with excellent sensitivity, LWR performance, and resolution.

Compound

A compound according to one embodiment of the invention is represented by the formula (i). Since the compound has the structure represented by the formula (i), the compound may suitably be used as a monomer compound for incorporating the structural unit (I) in a polymer.

Method for Producing Compound (i)

A method for producing the compound represented by the formula (i) according to one embodiment of the invention includes reacting the cyclic α,β-unsaturated ketone represented by the formula (a) with the organolithium compound represented by the formula (b) or the hydrogenation agent to obtain the cyclic unsaturated alcohol represented by the formula (c), and reacting the cyclic unsaturated alcohol represented by the formula (c) with the compound represented by the formula (d). The compound (i) is synthesized according to the following scheme, for example.

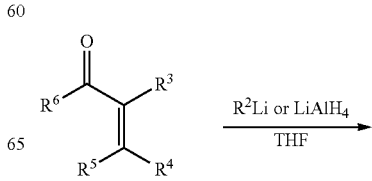

-continued

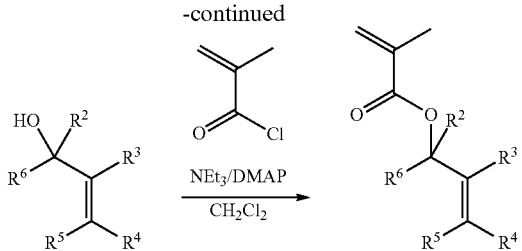

In the above scheme, $R^3$ to $R^6$ are the same as defined for the formula (i), and $R^2$ is a hydrogen atom, a methyl group, an ethyl group, or an i-propyl group.

The compound (i) can be easily synthesized by the above method.

The details of the polymer, the compound, and the method for producing the compound are the same as described above in connection with the polymer [A] included in the radiation-sensitive resin composition. Therefore, further description thereof is omitted.

EXAMPLES

The invention is further described below by way of examples. Note that the invention is not limited to the following examples. The property values were measured using the following methods.

Measurement of Mw and Mn

The Mw and the Mn of the polymer were measured by gel permeation chromatography (GPC) under the following conditions.

Column: G2000HXL×2, G3000HXL×1, G4000HXL×1 (manufactured by Tosoh Corporation)
Eluant: tetrahydrofuran
Column temperature: 40° C.
Flow rate: 1.0 ml/min
Detector: differential refractometer
Standard: monodisperse polystyrene $^1$H-NMR Analysis and $^{13}$C-NMR Analysis $^1$H-NMR analysis and $^{13}$C-NMR analysis of the compound, and $^{13}$C-NMR analysis for determining the content of each structural unit and the fluorine atom content in the polymer were performed using a nuclear magnetic resonance spectrometer ("JNM-ECX400" manufactured by JEOL Ltd.).

Synthesis of Compound (i)

A compound (i) was synthesized according to the following scheme.

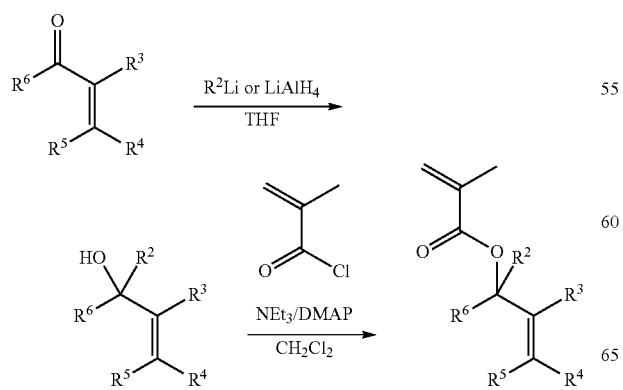

In the above scheme, $R^3$ to $R^6$ are the same as defined for the formula (i), and $R^2$ is a hydrogen atom, a methyl group, an ethyl group, or an i-propyl group.

Example 1

A recovery flask (1 L) was charged with 48.1 g (500 mmol) of 2-methylenecyclopentanone and 300 mL of THF. The mixture was cooled to −78° C. using a dry ice-methanol bath. A diethyl ether solution of methyllithium (525 mmol) was slowly added dropwise to the mixture. After stirring the mixture at −78° C. for 3 hours, and at room temperature for 3 hours, a small amount of water was added to the mixture to terminate the reaction. The mixture was subjected to extraction, washing, and purification by column chromatography to obtain 43.7 g of 1-methyl-2-methylenecyclopentanol (yield: 78%).

A recovery flask (1 L) was charged with 43.4 g (387 mmol) of 1-methyl-2-methylenecyclopentanol, 58.7 g (581 mmol) of triethylamine, 1.42 g (11.6 mmol) of N,N-dimethylaminopyridine, and 500 mL of dichloromethane. The mixture was cooled to 0° C. using an ice bath. 200 mL of a dichloromethane solution of 42.5 g (406 mmol) of methacryloyl chloride was slowly added dropwise to the mixture. After stirring the mixture at 0° C. for 30 minutes, and at room temperature for 3 hours, a small amount of water was added to the mixture to terminate the reaction. The mixture was subjected to extraction, washing, and purification by column chromatography to obtain 59.3 g of 1-methyl-2-methylenecyclopentan-1-ylmethacrylate represented by the following formula (M-1) (yield: 85%) (total yield: 66%).

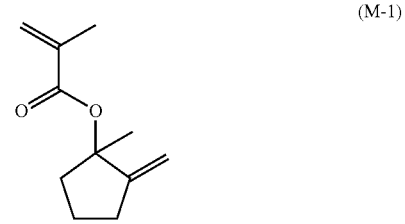

(M-1)

Example 2

1-Methyl-2-methylenecyclohexan-1-ylmethacrylate represented by the following formula (M-2) was synthesized in the same manner as in Example 1, except that 2-methylenecyclohexanone was used as the starting material instead of 2-methylenecyclopentanone (total yield: 52%).

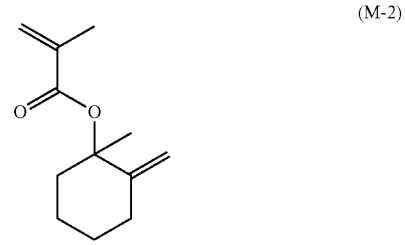

(M-2)

Example 3

1-Ethyl-2-methylenecyclopentan-1-yl methacrylate represented by the following formula (M-3) was synthesized in the same manner as in Example 1, except that ethyllithium was used as the reaction reagent instead of methyllithium (total yield: 49%).

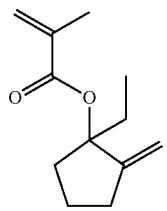
(M-3)

Example 4

1-Ethyl-2-methylenecyclohexan-1-ylmethacrylate represented by the following formula (M-4) was synthesized in the same manner as in Example 2, except that ethyllithium was used as the reaction reagent instead of methyllithium (total yield: 50%).

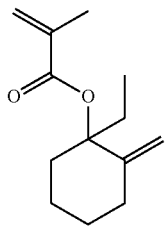
(M-4)

Example 5

1-Isopropyl-2-methylenecyclopentan-1-yl methacrylate represented by the following formula (M-5) was synthesized in the same manner as in Example 1, except that isopropyllithium was used as the reaction reagent instead of methyllithium (total yield: 25%).

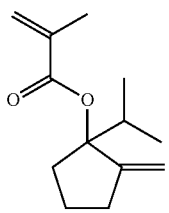
(M-5)

Example 6

1-Isopropyl-2-methylenecyclohexan-1-ylmethacrylate represented by the following formula (M-6) was synthesized in the same manner as in Example 2, except that isopropyllithium was used as the reaction reagent instead of methyllithium (total yield: 27%).

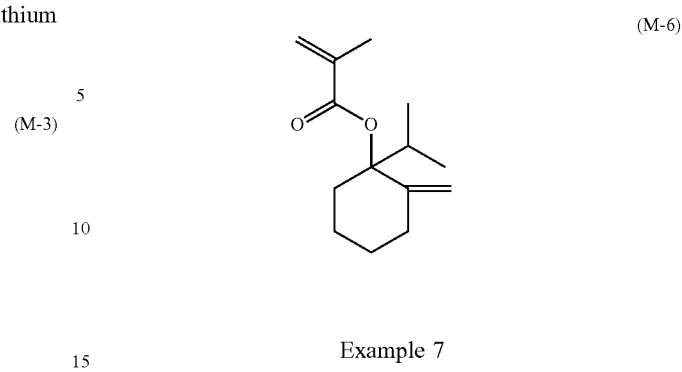
(M-6)

Example 7

A recovery flask (1 L) was charged with 41 g (500 mmol) of 2-cyclopenten-1-one and 300 mL of THF. The mixture was cooled to 0° C. using an ice water bath. A suspension prepared by suspending 28.5 g (750 mmol) of lithium aluminum hydride in 150 ml of THF was slowly added dropwise to the mixture. After the dropwise addition, the ice water bath was removed, and the mixture was stirred at room temperature for 12 hours. After cooling the mixture to 0° C. using an ice water bath, water and a 10 mass % sodium hydroxide aqueous solution were added to the mixture to terminate the reaction. The mixture was subjected to extraction, washing, and purification by column chromatography to obtain 37 g of 2-cyclopenten-1-ol (yield: 88%).

A recovery flask (1 L) was charged with 37 g (440 mmol) of 2-cyclopenten-1-ol, 66.8 g (660 mmol) of triethylamine, 1.61 g (13.2 mmol) of N,N-dimethylaminopyridine, and 500 mL of dichloromethane. The mixture was cooled to 0° C. using an ice bath. 200 mL of a dichloromethane solution of 48.3 g (462 mmol) of methacryloyl chloride was slowly added dropwise to the mixture. After stirring the mixture at 0° C. for 30 minutes, and at room temperature for 3 hours, a small amount of water was added to the mixture to terminate the reaction. The mixture was subjected to extraction, washing, and purification by column chromatography to obtain 45.5 g of 2-cyclopenten-1yl methacrylate represented by the following formula (M-7) (yield: 68%) (total yield: 60%).

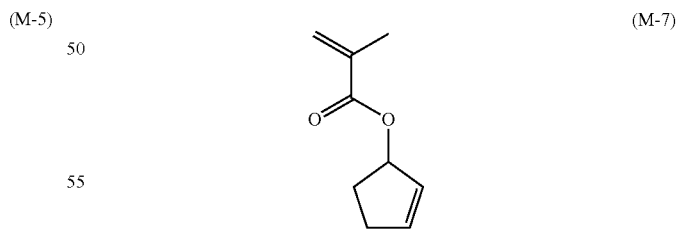
(M-7)

Example 8

2-Cyclohexen-1-yl methacrylate represented by the following formula (M-8) was synthesized in the same manner as in Example 7, except that 2-cyclohexen-1-one was used as the starting material instead of 2-cyclopenten-1-one (total yield: 55%).

(M-8) 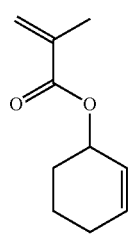
Examples 9 to 19
The compounds respectively represented by the following formulas (M-9) to (M-18) and (M-25) were synthesized in the same manner as in Example 7, except that each commercially available alcohol was used as the starting material.
(M-9) 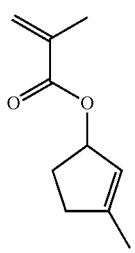
(M-10) 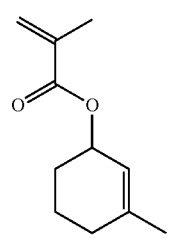
(M-11) 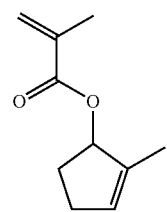
(M-12) 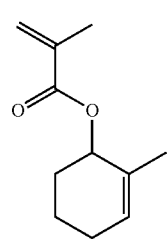
(M-13) 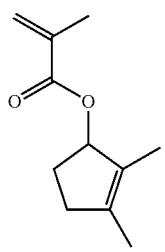
(M-14) 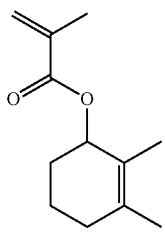
(M-15) 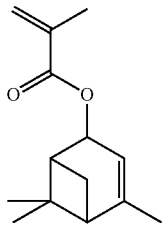
(M-16) 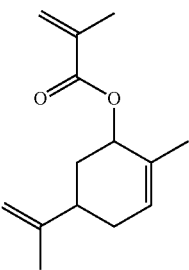
(M-17) 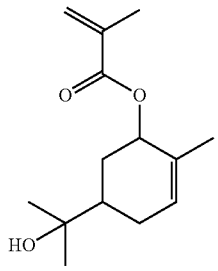
(M-18) 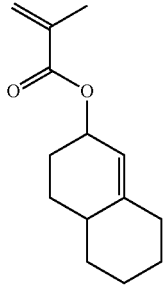

(M-25)

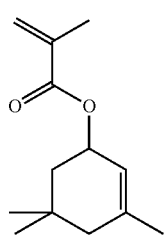

Example 20

2-Methylenecyclopentan-1-ylmethacrylate represented by the following formula (M-19) was synthesized in the same manner as in Example 7, except that 2-methylenecyclopentanone was used as the starting material instead of 2-cyclopenten-1-one (total yield: 46%).

(M-19)

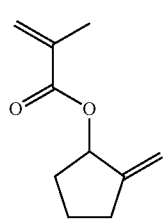

Example 21

2-Methylenecyclohexan-1-yl methacrylate represented by the following formula (M-20) was synthesized in the same manner as in Example 7, except that 2-methylenecyclohexanone was used as the starting material instead of 2-cyclopenten-1-one (total yield: 46%).

(M-20)

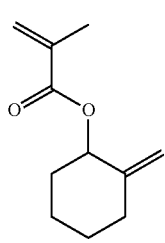

Examples 22 and 23

The compounds respectively represented by the following formulas (M-21) and (M-22) were synthesized in the same manner as in Example 7, except that the starting material and the reaction reagent were appropriately selected.

(M-21)

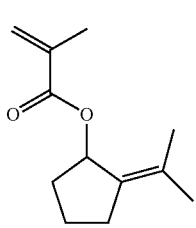

(M-22)

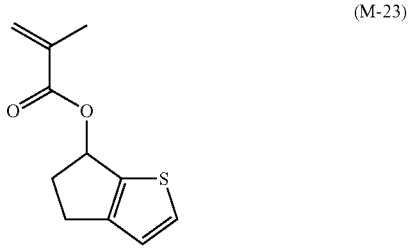

Example 24

The compound represented by the following formula (M-23) was synthesized in the same manner as in Example 7, except that 4H-cyclopenta[b]thiophen-6(5H)-one was used as the starting material instead of 2-cyclopenten-1-one (total yield: 34%).

(M-23)

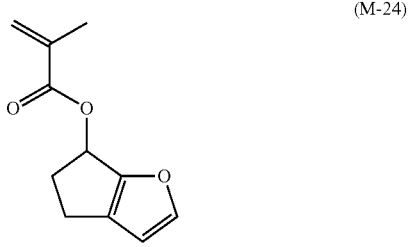

Example 25

The compound represented by the following formula (M-24) was synthesized in the same manner as in Example 7, except that 4H-cyclopenta[b]furan-6(5H)-one was used as the starting material instead of 2-cyclopenten-1-one (total yield: 39%).

(M-24)

Synthesis of Polymer

The monomers used to synthesize the polymer [A] and the additional polymer [E] are shown below. Note that the compounds (M-1) to (M-25) produce the structural unit (I), the compound (M-26) produces the structural unit (IV), the compound (M-27) produces the structural unit (VI), and the compound (M-28) produces the structural unit (II).

(M-26)

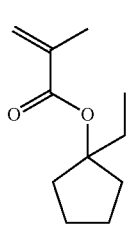

-continued

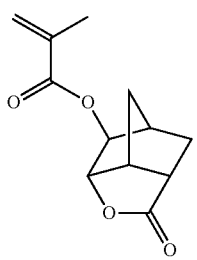
(M-27)

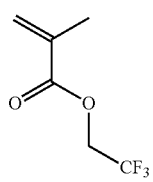
(M-28)

Synthesis of Polymer [A]

Example 26

8.56 g (50 mol %) of the compound (M-1) and 11.44 g (50 mol %) of the compound (M-27) were dissolved in 40 g of 2-butanone, and 0.85 g of AIBN (initiator) was dissolved in the solution to prepare a monomer solution. A three-necked flask (100 ml) was charged with 20 g of 2-butanone, purged with nitrogen for 30 minutes, and heated to 80° C. with stirring. The monomer solution was added dropwise to the flask over 3 hours using a dropping funnel. The monomers were polymerized for 6 hours from the start of dropwise addition of the monomer solution. After completion of polymerization, the polymer solution was cooled with water to 30° C. or less. The cooled polymer solution was added to 400 g of methanol, and a precipitate (white powder) was filtered off. The white powder was washed twice with 80 g of methanol, filtered off, and dried at 50° C. for 17 hours to obtain a white powdery polymer (A-1) (15.2 g, yield: 76%). The polymer (A-1) had an Mw of 7100 and a dispersity (Mw/Mn) of 1.53. As a result of $^{13}$C-NMR analysis, it was found that the content of the structural unit (I) and the content of the structural unit (VI) in the polymer (A-1) were 50.3 mol % and 49.7 mol %, respectively. The content of low-molecular-weight components (i.e., components having a molecular weight of less than 1000) in the polymer (A-1) was 0.04 mass %.

Examples 27 to 53 and Synthesis Example 1

A polymer was synthesized in the same manner as in Example 26, except that the types and the amounts of the monomers were changed as shown in Table 1. The yield (%), the Mw, and the dispersity (Mw/Mn) of the resulting polymer are also shown in Table 1. Note that "-" in Table 1 indicates that the corresponding component was not used.

TABLE 1

| | Component [A] | Monomer that produces structural unit (I) | | | Monomer that produces structural unit (II) | | | Monomer that produces structural unit (VI) | | |
|---|---|---|---|---|---|---|---|---|---|---|
| | | Type | Amount (mol %) | Structural unit content (mol %) | Type | Amount (mol %) | Structural unit content (mol %) | Type | Amount (mol %) | Structural unit content (mol %) |
| Example 26 | A-1 | M-1 | 50 | 50.1 | — | — | — | M-27 | 50 | 49.9 |
| Example 27 | A-2 | M-2 | 50 | 50.1 | — | — | — | M-27 | 50 | 49.9 |
| Example 28 | A-3 | M-3 | 50 | 49.8 | — | — | — | M-27 | 50 | 50.2 |
| Example 29 | A-4 | M-4 | 50 | 50.0 | — | — | — | M-27 | 50 | 50.0 |
| Example 30 | A-5 | M-5 | 50 | 48.8 | — | — | — | M-27 | 50 | 51.2 |
| Example 31 | A-6 | M-6 | 50 | 48.6 | — | — | — | M-27 | 50 | 51.4 |
| Example 32 | A-10 | M-7 | 50 | 49.1 | — | — | — | M-27 | 50 | 50.9 |
| Example 33 | A-11 | M-8 | 50 | 48.1 | — | — | — | M-27 | 50 | 51.9 |
| Example 34 | A-12 | M-9 | 50 | 48.3 | — | — | — | M-27 | 50 | 51.7 |
| Example 35 | A-13 | M-10 | 50 | 49.1 | — | — | — | M-27 | 50 | 50.9 |
| Example 36 | A-14 | M-11 | 50 | 50.1 | — | — | — | M-27 | 50 | 49.9 |
| Example 37 | A-15 | M-12 | 50 | 50.1 | — | — | — | M-27 | 50 | 49.9 |
| Example 38 | A-16 | M-13 | 50 | 49.8 | — | — | — | M-27 | 50 | 50.2 |
| Example 39 | A-17 | M-14 | 50 | 50.0 | — | — | — | M-27 | 50 | 50.0 |
| Example 40 | A-18 | M-15 | 50 | 48.8 | — | — | — | M-27 | 50 | 51.2 |
| Example 41 | A-19 | M-16 | 50 | 48.7 | — | — | — | M-27 | 50 | 51.3 |
| Example 42 | A-20 | M-17 | 50 | 49.1 | — | — | — | M-27 | 50 | 50.9 |
| Example 43 | A-21 | M-18 | 50 | 48.8 | — | — | — | M-27 | 50 | 51.2 |
| Example 44 | A-22 | M-19 | 50 | 48.8 | — | — | — | M-27 | 50 | 51.2 |
| Example 45 | A-23 | M-20 | 50 | 48.3 | — | — | — | M-27 | 50 | 51.7 |
| Example 46 | A-24 | M-21 | 50 | 49.1 | — | — | — | M-27 | 50 | 50.9 |
| Example 47 | A-25 | M-22 | 50 | 48.8 | — | — | — | M-27 | 50 | 51.2 |
| Example 48 | A-26 | M-23 | 50 | 45.8 | — | — | — | M-27 | 50 | 54.2 |
| Example 49 | A-27 | M-24 | 50 | 48.3 | — | — | — | M-27 | 50 | 51.7 |
| Example 50 | A-28 | M-25 | 50 | 49.2 | — | — | — | M-27 | 50 | 50.8 |
| Example 51 | A-29 | M-9 | 30 | 29.8 | — | — | — | M-27 | 55 | 55.3 |
| | | M-10 | 15 | 14.9 | — | — | — | | | |
| Example 52 | A-30 | M-10 | 20 | 20.1 | — | — | — | M-27 | 60 | 59.8 |
| Example 53 | A-31 | M-6 | 70 | 69.9 | M-28 | 30 | 30.1 | — | — | — |
| Synthesis Example 1 | a-1 | — | — | — | — | — | — | M-27 | 73 | 54.1 |

TABLE 1-continued

| | Monomer that produces structural unit (IV) | | | Content of low- | | |
| --- | --- | --- | --- | --- | --- | --- |
| | Type | Amount (mol %) | Structural unit content (mol %) | Yield (%) | molecular-weight components (mass %) | Mw | Mw/Mn |
| Example 26 | — | — | — | 73 | 0.04 | 7100 | 1.51 |
| Example 27 | — | — | — | 70 | 0.04 | 7200 | 1.51 |
| Example 28 | — | — | — | 74 | 0.04 | 7100 | 1.52 |
| Example 29 | — | — | — | 77 | 0.05 | 7000 | 1.53 |
| Example 30 | — | — | — | 74 | 0.04 | 7100 | 1.54 |
| Example 31 | — | — | — | 75 | 0.05 | 7100 | 1.54 |
| Example 32 | — | — | — | 67 | 0.04 | 7200 | 1.55 |
| Example 33 | — | — | — | 70 | 0.04 | 7200 | 1.52 |
| Example 34 | — | — | — | 73 | 0.04 | 7000 | 1.54 |
| Example 35 | — | — | — | 69 | 0.05 | 7000 | 1.53 |
| Example 36 | — | — | — | 73 | 0.04 | 7100 | 1.51 |
| Example 37 | — | — | — | 70 | 1.51 | 7200 | 1.51 |
| Example 38 | — | — | — | 74 | 1.51 | 7100 | 1.52 |
| Example 39 | — | — | — | 77 | 0.05 | 7000 | 1.53 |
| Example 40 | — | — | — | 74 | 0.04 | 7100 | 1.54 |
| Example 41 | — | — | — | 66 | 0.05 | 7100 | 1.51 |
| Example 42 | — | — | — | 65 | 0.05 | 7200 | 1.54 |
| Example 43 | — | — | — | 68 | 0.05 | 7100 | 1.53 |
| Example 44 | — | — | — | 70 | 0.04 | 7200 | 1.51 |
| Example 45 | — | — | — | 67 | 1.51 | 7100 | 1.52 |
| Example 46 | — | — | — | 65 | 1.51 | 7200 | 1.54 |
| Example 47 | — | — | — | 68 | 1.51 | 7100 | 1.53 |
| Example 48 | — | — | — | 63 | 0.05 | 7000 | 1.55 |
| Example 49 | — | — | — | 67 | 0.05 | 7100 | 1.52 |
| Example 50 | — | — | — | 64 | 0.05 | 7000 | 1.52 |
| Example 51 | — | — | — | 71 | 0.04 | 7100 | 1.53 |
| Example 52 | M-26 | 20 | 20.1 | 73 | 0.04 | 7100 | 1.51 |
| Example 53 | — | — | — | 68 | 0.04 | 7200 | 2.01 |
| Synthesis Example 1 | M-26 | 50 | 45.9 | 61 | 1.52 | 6900 | 1.54 |

Synthesis of Additional Polymer [E]

Synthesis Example 2

79.9 g (70 mol %) of the compound (M-26) and 20.91 g (30 mol %) of the compound (M-28) were dissolved in 100 g of 2-butanone, and 4.77 g of dimethyl 2,2'-azobisisobutyrate was dissolved in the solution to prepare a monomer solution. A three-necked flask (1000 mL) was charged with 100 g of 2-butanone, purged with nitrogen for 30 minutes, and heated to 80° C. with stirring. The monomer solution was added dropwise to the flask over 3 hours using a dropping funnel. The monomers were polymerized for 6 hours from the start of dropwise addition of the monomer solution. After completion of polymerization, the polymer solution was cooled with water to 30° C. or less. The polymer solution was put in a separating funnel (2 L), and homogeneously diluted with 150 g of n-hexane. After the addition of 600 g of methanol, the components were mixed. After the addition of 30 g of distilled water, the mixture was stirred, and allowed to stand for 30 minutes. The lower layer was collected, and dissolved in propylene glycol monomethyl ether acetate (yield: 60%). The resulting polymer (E-1) had an Mw of 7200, a dispersity (Mw/Mn) of 2.00, and a content of low-molecular-weight components of 0.07 mass %. As a result of $^{13}$C-NMR analysis, it was found that the content of the structural unit (IV) and the content of the structural unit (II) in the polymer (E-1) were 71.1 mol % and 28.9 mol %, respectively.

Preparation of Radiation-Sensitive Resin Composition

The following components were used to prepare each radiation-sensitive resin composition.

Acid Generator [B]

B-1: triphenylsulfonium 2-(adamantan-1-yl)-1,1-difluoroethane-1-sulfonate (compound represented by the following formula (B-1))

B-2: triphenylsulfonium 2-(adamantylcarbonyloxy)-1,1,3,3,3-pentafluoropropanesulfonate (compound represented by the following formula (B-2))

B-3: triphenylsulfonium norbornanesultonyloxycarbonyldifluoromethanesulfonate (compound represented by the following formula (B-3))

B-4: triphenylsulfonium 3-piperidylsulfonyl-1,1,2,2,3,3-hexafluoropropane-1-sulfonate (compound represented by the following formula (B-4))

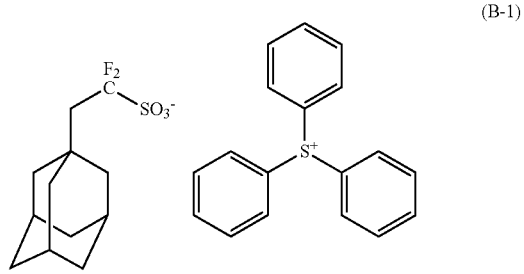

(B-1)

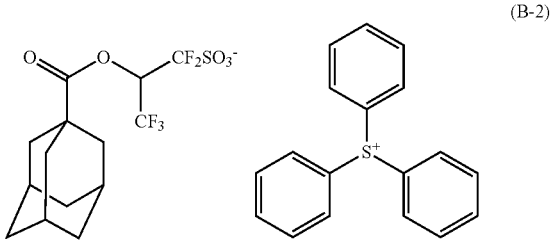

(B-2)

-continued

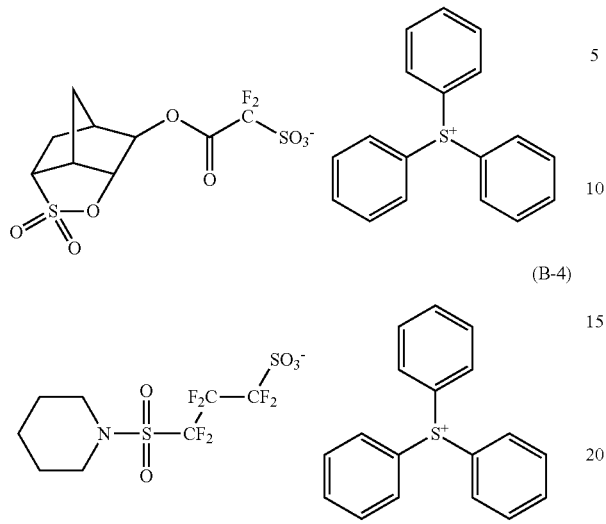
(B-3)
(B-4)
(D-4)
(D-5)

Solvent [C]
C-1: propylene glycol monomethyl ether acetate
C-2: cyclohexanone
Acid Diffusion Controller [D]
D-1: triphenylsulfonium 10-camphorsulfonate (compound represented by the following formula (D-1))
D-2: triphenylsulfonium salicylate (compound represented by the following formula (D-2))
D-3: N-(undecylcarbonyloxyethyl)morpholine (compound represented by the following formula (D-3))
D-4: 2,6-diisopropylaniline (compound represented by the following formula (D-4))
D-5: tri-n-pentylamine (compound represented by the following formula (D-5))

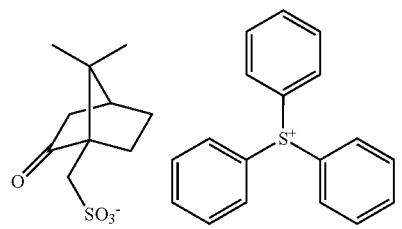
(D-1)

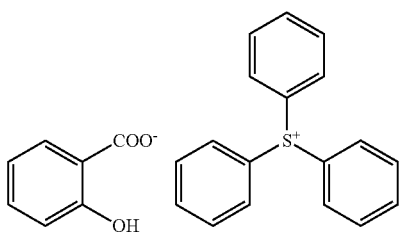
(D-2)

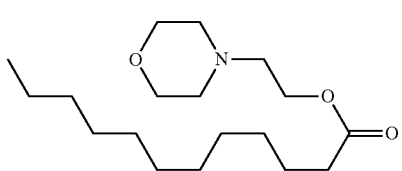
(D-3)

Uneven Distribution Promoter [G]
G-1: γ-butyrolactone

Example 54

100 parts by mass of the polymer (A-1) (polymer [A]), 8.5 parts by mass of the acid generator (B-1) (acid generator [B]), 2240 parts by mass of the solvent (C-1) (solvent [C]), 960 parts by mass of the solvent (C-2) (solvent [C]), 2.3 parts by mass of the acid diffusion controller (D-1) (acid diffusion controller [D]), 3 parts by mass of the polymer (E-1) (additional polymer [E]), and 3.0 parts by mass of the uneven distribution promoter (G-1) (uneven distribution promoter [G]) were mixed to prepare a radiation-sensitive resin composition (J-1).

Examples 55 to 81 and Comparative Examples 1 to 5

A radiation-sensitive resin composition was prepared in the same manner as in Example 54, except that the types and the amounts of the components were changed as shown in Table 2. The type and the amount of each solvent [C] were the same as in Example 54. Note that "-" in Table 2 indicates that the corresponding component was not used.
Formation of Resist Pattern
Formation of Resist Pattern Using Alkali Development, and Evaluation of Radiation-Sensitive Resin Composition A lower-layer antireflective film-forming composition ("ARC66" manufactured by Brewer Science) was applied to a 12-inch silicon wafer using a spin coater ("CLEAN TRACK ACT 12" manufactured by Tokyo Electron Ltd.), and baked at 205° C. for 60 seconds to form a lower-layer antireflective film having a thickness of 105 nm. The radiation-sensitive resin composition was applied to the lower-layer antireflective film using the above spin coater, and prebaked (PB) at 90° C. for 60 seconds. The radiation-sensitive resin composition was cooled at 23° C. for 30 seconds to form a resist film having a thickness of 90 nm. The resist film was exposed via a 40 nm line-and-space (1L1S) mask pattern using an ArF immersion scanner ("NSR-S610C" manufactured by Nikon Corporation) (NA=1.3, Dipole (σ 0.977/0.782)). The resist film was then subjected to PEB at 85° C. for 60 seconds, developed using a 2.38 mass % TMAH aqueous solution, rinsed with water, and dried to form a positive-tone resist pattern.

Evaluation

The radiation-sensitive resin composition was evaluated by measurement using the resulting resist pattern. The results are shown in Table 2. A scanning electron microscope ("S-9380" manufactured by Hitachi High-Technologies Corporation) was used for the measurement.

Sensitivity

An optimum dose (mJ/cm$^2$) at which a 1:1 line-and-space (1L/1S) pattern having a line width of 90 nm was formed via a 40 nm 1:1 line-and-space mask was taken as the sensitivity. The sensitivity is high when the measured value is small. A case where the sensitivity was 35 mJ/cm$^2$ or less was evaluated as acceptable.

LWR Performance

The resist pattern was observed from above using the above scanning electron microscope. The line width of the resist pattern was measured at an arbitrary 50 points, and the 3σ value was calculated from the distribution of the measured values, and taken as the LWR performance (nm). The LWR performance is good when the measured value is small. A case where the LWR performance was 3.8 nm or less was evaluated as acceptable.

Resolution

The minimum dimensions of the resist pattern resolved at the optimum dose were taken as the resolution (nm). The resolution is good when the measured value is small. A case where the resolution was 35 nm or less was evaluated as acceptable.

Formation of Resist Pattern Using Organic Solvent Development, and Evaluation of Radiation-Sensitive Resin Composition Radiation-sensitive resin compositions were prepared in the same manner as in Examples 54 to 81 and Comparative Examples 1 to 5 (see Table 2). A resist pattern was formed, and the radiation-sensitive resin composition was evaluated in the same manner as described above, except that n-butyl acetate was used as the developer instead of a 2.38 mass % TMAH aqueous solution, and the rinse step was not performed. The results are shown in Table 2.

TABLE 2

| | Radiation-sensitive resin composition | Composition of radiation-sensitive resin composition | | | | | | | | | Evaluation results | | | | | |
|---|---|---|---|---|---|---|---|---|---|---|---|---|---|---|---|---|
| | | Component [A] | | Acid generator [B] | | Acid diffusion controller [D] | | Additional polymer [E] | | PEB temp. (°C.) | TMAH development | | | Organic solvent development | | |
| | | | | | | | | | | | | | | LWR | | |
| | | Type | Amount (parts by mass) | Type | Amount (parts by mass) | Type | Amount (parts by mass) | Type | Amount (parts by mass) | | Sensitivity (mJ/cm$^2$) | LWR performance (nm) | Resolution (nm) | Sensitivity (mJ/cm$^2$) | performance (nm) | Resolution (nm) |
| Example 54 | J-1 | A-1 | 100 | B-1 | 8.5 | D-1 | 2.3 | E-1 | 3 | 85 | 20 | 3.76 | 33 | 23 | 3.61 | 34 |
| Example 55 | J-2 | A-2 | 100 | B-1 | 8.5 | D-1 | 2.3 | E-1 | 3 | 85 | 19 | 3.69 | 32 | 22 | 3.54 | 33 |
| Example 56 | J-3 | A-3 | 100 | B-1 | 8.5 | D-1 | 2.3 | E-1 | 3 | 85 | 18 | 3.71 | 32 | 21 | 3.56 | 33 |
| Example 57 | J-4 | A-4 | 100 | B-1 | 8.5 | D-1 | 2.3 | E-1 | 3 | 85 | 18 | 3.71 | 33 | 21 | 3.56 | 34 |
| Example 58 | J-5 | A-5 | 100 | B-1 | 8.5 | D-1 | 2.3 | E-1 | 3 | 85 | 15 | 3.73 | 31 | 18 | 3.58 | 32 |
| Example 59 | J-6 | A-6 | 100 | B-1 | 8.5 | D-1 | 2.3 | E-1 | 3 | 85 | 15 | 3.68 | 32 | 18 | 3.53 | 33 |
| Example 60 | J-10 | A-10 | 100 | B-1 | 8.5 | D-1 | 2.3 | E-1 | 3 | 85 | 35 | 3.78 | 30 | 38 | 3.63 | 31 |
| Example 61 | J-11 | A-11 | 100 | B-1 | 8.5 | D-1 | 2.3 | E-1 | 3 | 85 | 35 | 3.79 | 31 | 38 | 3.64 | 32 |
| Example 62 | J-12 | A-12 | 100 | B-1 | 8.5 | D-1 | 2.3 | E-1 | 3 | 85 | 24 | 3.37 | 26 | 27 | 3.22 | 27 |
| Example 63 | J-13 | A-13 | 100 | B-1 | 8.5 | D-1 | 2.3 | E-1 | 3 | 85 | 23 | 3.38 | 27 | 26 | 3.23 | 28 |
| Example 64 | J-14 | A-14 | 100 | B-1 | 8.5 | D-1 | 2.3 | E-1 | 3 | 85 | 23 | 3.51 | 32 | 26 | 3.36 | 33 |
| Example 65 | J-15 | A-15 | 100 | B-1 | 8.5 | D-1 | 2.3 | E-1 | 3 | 85 | 24 | 3.52 | 31 | 27 | 3.37 | 32 |
| Example 66 | J-16 | A-16 | 100 | B-1 | 8.5 | D-1 | 2.3 | E-1 | 3 | 85 | 21 | 3.52 | 30 | 24 | 3.37 | 31 |
| Example 67 | J-17 | A-17 | 100 | B-1 | 8.5 | D-1 | 2.3 | E-1 | 3 | 85 | 21 | 3.51 | 30 | 24 | 3.36 | 31 |
| Example 68 | J-18 | A-18 | 100 | B-1 | 8.5 | D-1 | 2.3 | E-1 | 3 | 85 | 22 | 3.38 | 32 | 25 | 3.23 | 33 |
| Example 69 | J-19 | A-19 | 100 | B-1 | 8.5 | D-1 | 2.3 | E-1 | 3 | 85 | 23 | 3.55 | 32 | 26 | 3.40 | 33 |
| Example 70 | J-20 | A-20 | 100 | B-1 | 8.5 | D-1 | 2.3 | E-1 | 3 | 85 | 22 | 3.66 | 32 | 25 | 3.51 | 33 |
| Example 71 | J-21 | A-21 | 100 | B-1 | 8.5 | D-1 | 2.3 | E-1 | 3 | 85 | 23 | 3.67 | 31 | 26 | 3.52 | 32 |
| Example 72 | J-22 | A-22 | 100 | B-1 | 8.5 | D-1 | 2.3 | E-1 | 3 | 85 | 29 | 3.66 | 31 | 32 | 3.51 | 32 |
| Example 73 | J-23 | A-23 | 100 | B-1 | 8.5 | D-1 | 2.3 | E-1 | 3 | 85 | 30 | 3.68 | 30 | 33 | 3.53 | 31 |
| Example 74 | J-24 | A-24 | 100 | B-1 | 8.5 | D-1 | 2.3 | E-1 | 3 | 85 | 22 | 3.66 | 31 | 25 | 3.51 | 32 |
| Example 75 | J-25 | A-25 | 100 | B-1 | 8.5 | D-1 | 2.3 | E-1 | 3 | 85 | 23 | 3.71 | 30 | 26 | 3.56 | 31 |
| Example 76 | J-26 | A-26 | 100 | B-1 | 8.5 | D-1 | 2.3 | E-1 | 3 | 85 | 20 | 3.67 | 31 | 23 | 3.52 | 32 |
| Example 77 | J-27 | A-27 | 100 | B-1 | 8.5 | D-1 | 2.3 | E-1 | 3 | 85 | 21 | 3.69 | 31 | 24 | 3.54 | 32 |
| Example 78 | J-28 | A-28 | 100 | B-1 | 8.5 | D-1 | 2.3 | E-1 | 3 | 85 | 23 | 3.51 | 29 | 19 | 3.36 | 28 |
| Example 79 | J-29 | A-29 | 100 | B-1 | 8.5 | D-1 | 2.3 | E-1 | 3 | 85 | 23 | 3.40 | 27 | 19 | 3.25 | 28 |
| Example 80 | J-30 | A-30 | 100 | B-1 | 8.5 | D-1 | 2.3 | E-1 | 3 | 85 | 25 | 3.55 | 29 | 27 | 3.41 | 29 |
| Example 81 | J-31 | A-31 A-12 | 3 100 | B-1 | 8.5 | D-1 | 2.3 | — | — | 85 | 24 | 3.33 | 25 | 27 | 3.20 | 26 |
| Comparative Example 1 | CJ-1 | a-1 | 100 | B-1 | 8.5 | D-1 | 2.3 | E-1 | 3 | 85 | 22 | 4.01 | 36 | 25 | 3.86 | 37 |
| Comparative Example 2 | CJ-2 | a-1 | 100 | B-2 | 8.5 | D-2 | 2.3 | E-1 | 3 | 85 | 24 | 4.04 | 36 | 27 | 3.89 | 37 |
| Comparative Example 3 | CJ-3 | a-1 | 100 | B-3 | 8.5 | D-3 | 2.3 | E-1 | 3 | 85 | 20 | 4.08 | 37 | 23 | 3.93 | 38 |
| Comparative Example 4 | CJ-4 | a-1 | 100 | B-4 | 8.5 | D-4 | 2.3 | E-1 | 3 | 85 | 23 | 4.11 | 37 | 26 | 3.96 | 38 |
| Comparative Example 5 | CJ-5 | a-1 | 100 | B-1 | 8.5 | D-5 | 2.3 | E-1 | 3 | 85 | 24 | 4.14 | 37 | 27 | 3.99 | 38 |

Formation of Resist Pattern Using Electron Beam Irradiation

Preparation of Radiation-Sensitive Resin Composition

Example 82

100 parts by mass of the polymer (A-1) (polymer [A]), 20 parts by mass of the acid generator (B-1) (acid generator [B]), 4280 parts by mass of the solvent (C-1) (solvent [C]), 1830 parts by mass of the solvent (C-2) (solvent [C]), and 3.6 parts by mass of the acid diffusion controller (D-1) (acid diffusion controller [D]) were mixed to prepare a radiation-sensitive resin composition (J-32).

Examples 83 to 105 and Comparative Examples 6 to 10

A radiation-sensitive resin composition was prepared in the same manner as in Example 82, except that the types and the amounts of the components were changed as shown in Table 3.

Formation of Resist Pattern and Evaluation of Radiation-Sensitive Resin Composition The radiation-sensitive resin composition (see Table 3) was applied to an 8-inch silicon wafer using a spin coater ("CLEAN TRACK ACT 8" manufactured by Tokyo Electron Ltd.), and prebaked (PB) at 90° C. for 60 seconds. The radiation-sensitive resin composition was then cooled at 23° C. for 30 seconds to form a resist film having a thickness of 50 nm. The resist film was exposed to electron beams using an electron beam drawing system ("HL800D" manufactured by Hitachi, Ltd., output: 50 KeV, current density: 5.0 A/cm$^2$). The resist film was then subjected to PEB at 85° C. for 60 seconds, developed at 23° C. for 30 seconds using a 2.38 mass % TMAH aqueous solution, rinsed with water, and dried to form a positive-tone resist pattern. The resist pattern was evaluated in the same manner as in Examples 54 to 81 and Comparative Examples 1 to 5. The results are shown in Table 3. A case where the sensitivity was 50 mJ/cm$^2$ or less was evaluated as acceptable. A case where the LWR performance was 4.1 nm or less was evaluated as acceptable. A case where the resolution was 38 nm or less was evaluated as acceptable.

TABLE 3

| | Radiation-sensitive resin composition | Component [A] Type | Component [A] Amount (parts by mass) | Acid generator [B] Type | Acid generator [B] Amount (parts by mass) | Acid diffusion controller [D] Type | Acid diffusion controller [D] Amount (parts by mass) | PEB temp. (° C.) | Sensitivity (uC/cm$^2$) | LWR performance (nm) | Resolution (nm) |
|---|---|---|---|---|---|---|---|---|---|---|---|
| Example 82 | J-32 | A-1 | 100 | B-1 | 20 | D-1 | 3.6 | 85 | 35 | 4.01 | 37 |
| Example 83 | J-33 | A-2 | 100 | B-1 | 20 | D-1 | 3.6 | 85 | 34 | 3.94 | 36 |
| Example 84 | J-34 | A-3 | 100 | B-1 | 20 | D-1 | 3.6 | 85 | 33 | 3.96 | 36 |
| Example 85 | J-35 | A-4 | 100 | B-1 | 20 | D-1 | 3.6 | 85 | 33 | 3.96 | 37 |
| Example 86 | J-36 | A-5 | 100 | B-1 | 20 | D-1 | 3.6 | 85 | 30 | 3.98 | 35 |
| Example 87 | J-37 | A-6 | 100 | B-1 | 20 | D-1 | 3.6 | 85 | 30 | 3.93 | 36 |
| Example 88 | J-38 | A-10 | 100 | B-1 | 20 | D-1 | 3.6 | 85 | 50 | 4.03 | 34 |
| Example 89 | J-39 | A-11 | 100 | B-1 | 20 | D-1 | 3.6 | 85 | 50 | 4.04 | 35 |
| Example 90 | J-40 | A-12 | 100 | B-1 | 20 | D-1 | 3.6 | 85 | 39 | 3.62 | 30 |
| Example 91 | J-41 | A-13 | 100 | B-1 | 20 | D-1 | 3.6 | 85 | 38 | 3.63 | 31 |
| Example 92 | J-42 | A-14 | 100 | B-1 | 20 | D-1 | 3.6 | 85 | 38 | 3.76 | 36 |
| Example 93 | J-43 | A-15 | 100 | B-1 | 20 | D-1 | 3.6 | 85 | 39 | 3.77 | 35 |
| Example 94 | J-44 | A-16 | 100 | B-1 | 20 | D-1 | 3.6 | 85 | 36 | 3.77 | 34 |
| Example 95 | J-45 | A-17 | 100 | B-1 | 20 | D-1 | 3.6 | 85 | 36 | 3.76 | 34 |
| Example 96 | J-46 | A-18 | 100 | B-1 | 20 | D-1 | 3.6 | 85 | 37 | 3.63 | 36 |
| Example 97 | J-47 | A-19 | 100 | B-1 | 20 | D-1 | 3.6 | 85 | 38 | 3.8 | 36 |
| Example 98 | J-48 | A-20 | 100 | B-1 | 20 | D-1 | 3.6 | 85 | 37 | 3.91 | 36 |
| Example 99 | J-49 | A-21 | 100 | B-1 | 20 | D-1 | 3.6 | 85 | 38 | 3.92 | 35 |
| Example 100 | J-50 | A-22 | 100 | B-1 | 20 | D-1 | 3.6 | 85 | 44 | 3.91 | 35 |
| Example 101 | J-51 | A-23 | 100 | B-1 | 20 | D-1 | 3.6 | 85 | 45 | 3.93 | 34 |
| Example 102 | J-52 | A-24 | 100 | B-1 | 20 | D-1 | 3.6 | 85 | 37 | 3.91 | 35 |
| Example 103 | J-53 | A-25 | 100 | B-1 | 20 | D-1 | 3.6 | 85 | 38 | 3.96 | 34 |
| Example 104 | J-54 | A-26 | 100 | B-1 | 20 | D-1 | 3.6 | 85 | 35 | 3.92 | 35 |
| Example 105 | J-55 | A-27 | 100 | B-1 | 20 | D-1 | 3.6 | 85 | 36 | 3.94 | 35 |
| Comparative Example 6 | CJ-6 | A-28 | 100 | B-1 | 20 | D-1 | 3.6 | 85 | 37 | 4.26 | 40 |
| Comparative Example 7 | CJ-7 | A-28 | 100 | B-2 | 20 | D-2 | 3.6 | 85 | 39 | 4.29 | 40 |
| Comparative Example 8 | CJ-8 | A-28 | 100 | B-3 | 20 | D-3 | 3.6 | 85 | 35 | 4.33 | 40 |
| Comparative Example 9 | CJ-9 | A-28 | 100 | B-1 | 20 | D-4 | 3.6 | 85 | 38 | 4.36 | 40 |
| Comparative Example 10 | CJ-10 | A-28 | 100 | B-1 | 20 | D-5 | 3.6 | 85 | 39 | 4.39 | 40 |

The embodiments of the invention thus provide a radiation-sensitive resin composition that makes it possible to reduce the PEB temperature, and can form a resist pattern with excellent sensitivity, LWR performance, and resolution, a polymer that may suitably be used as a component of the radiation-sensitive resin composition, a compound that may suitably be used for the polymer, and a method for producing the compound. Therefore, the radiation-sensitive resin composition and the like may suitably be used for lithography that will be required to achieve a further reduction in line width.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
a polymer that comprises a structural unit represented by formula (1-1); and
an acid generator,

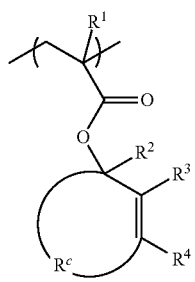

(1-1)

wherein:
$R^1$ is a hydrogen atom, a fluorine atom, a methyl group, or a trifluoromethyl group;
$R^2$ is a hydrogen atom;
$R^c$ is an organic group to form a cyclopentene structure or a cyclohexene structure together with the carbon atom bonded to $R^2$, with the carbon atom bonded to $R^3$, and with the carbon atom bonded to $R^4$, wherein the cyclopentene structure or the cyclohexene structure does not comprise —CO— or —CS— between carbon atoms included in the cyclopentene structure or the cyclohexene structure; and
$R^3$ and $R^4$ are each independently a hydrogen atom, a monovalent chain hydrocarbon group, a monovalent alicyclic hydrocarbon group, or a monovalent aromatic hydrocarbon group, wherein at least one hydrogen atom of the monovalent chain hydrocarbon group, the monovalent alicyclic hydrocarbon group, or the monovalent aromatic hydrocarbon group represented by $R^3$ or $R^4$ is optionally substituted with a fluorine atom, and in a case where $R^c$ forms the cyclohexene structure, at least one of $R^3$ and $R^4$ is a monovalent chain hydrocarbon group, a monovalent alicyclic hydrocarbon group, or a monovalent aromatic hydrocarbon group; or
$R^4$ is bonded to $R^3$ to form an alicyclic structure or an aromatic heterocyclic structure together with the carbon atom bonded to $R^3$ and with the carbon atom bonded to $R^4$; or
$R^3$ is a hydrogen atom, a monovalent chain hydrocarbon group, a monovalent alicyclic hydrocarbon group, or a monovalent aromatic hydrocarbon group, wherein at least one hydrogen atom of the monovalent chain hydrocarbon group, the monovalent alicyclic hydrocarbon group, or the monovalent aromatic hydrocarbon group represented by $R^3$ is optionally substituted with a fluorine atom, and $R^4$ is bonded to $R^c$ to form an alicyclic structure or an aromatic heterocyclic structure together with the carbon atom bonded to $R^4$.

2. A resist pattern-forming method comprising:
applying the radiation-sensitive resin composition according to claim 1 to form a resist film on a substrate;
exposing the resist film to ultraviolet rays, deep ultraviolet rays, extreme ultraviolet light, X-rays or charged particle rays;
heating the exposed resist film; and
developing the heated resist film to produce a pattern.

3. The resist pattern-forming method according to claim 2, wherein the exposed resist film is heated at 90° C. or less.

4. The radiation-sensitive resin composition according to claim 1, wherein $R^c$ forms the cyclopentene structure, and $R^3$ and $R^4$ are each independently a hydrogen atom, a monovalent chain hydrocarbon group, or a monovalent alicyclic hydrocarbon group.

5. The radiation-sensitive resin composition according to claim 1, wherein $R^c$ forms the cyclohexene structure, $R^3$ and $R^4$ are each independently a hydrogen atom, a monovalent chain hydrocarbon group or a monovalent alicyclic hydrocarbon group, and at least one of $R^3$ and $R^4$ is a monovalent chain hydrocarbon group, or a monovalent alicyclic hydrocarbon group.

6. The radiation-sensitive resin composition according to claim 1, wherein $R^c$ forms the cyclopentene structure, and $R^3$ and $R^4$ are each independently a hydrogen atom or a monovalent chain hydrocarbon group.

7. The radiation-sensitive resin composition according to claim 1, wherein $R^c$ forms the cyclohexene structure, and $R^3$ and $R^4$ are each independently a hydrogen atom or a monovalent chain hydrocarbon group, and at least one of $R^3$ and $R^4$ is a monovalent chain hydrocarbon group.

8. The radiation-sensitive resin composition according to claim 1, wherein the alicyclic structure formed by $R^3$ and $R^4$ is an alicyclic hydrocarbon structure or an aliphatic heterocyclic structure.

9. The radiation-sensitive resin composition according to claim 1, wherein the aromatic heterocyclic structure formed by $R^3$ and $R^4$ is a thiophene structure or a furan structure.

10. The radiation-sensitive resin composition according to claim 1, wherein the alicyclic structure formed by $R^4$ and $R^C$ is a cyclopentane structure or a cyclohexane structure.

11. The radiation-sensitive resin composition according to claim 1, wherein a content of the structural unit represented by formula (1-1) in the polymer is from 10 to 80 mol % based on total structural units included in the polymer.

12. The radiation-sensitive resin composition according to claim 1, wherein a content of the structural unit represented by formula (1-1) in the polymer is from 20 to 70 mol % based on total structural units included in the polymer.

13. The radiation-sensitive resin composition according to claim 1, wherein a content of the structural unit represented by formula (1-1) in the polymer is from 30 to 60 mol % based on total structural units included in the polymer.

14. The radiation-sensitive resin composition according to claim 1, wherein the polymer further comprises at least one structural unit selected from the group consisting of a structural unit that comprises a lactone structure and a structural unit that comprises a cyclic carbonate structure.

15. The radiation-sensitive resin composition according to claim 1, wherein the polymer further comprises a structural unit that comprises a fluorine atom.

16. The radiation-sensitive resin composition according to claim 1, wherein the structural unit represented by formula (1-1) comprises a fluorine atom.

17. The radiation-sensitive resin composition according to claim 1, further comprising a solvent.

* * * * *